United States Patent
Smith

(12) 
(10) Patent No.: US 10,400,967 B2
(45) Date of Patent: Sep. 3, 2019

(54) OPHTHALMIC ILLUMINATION SYSTEM WITH CONTROLLED CHROMATICITY

(71) Applicant: NOVARTIS AG, Basel (CH)

(72) Inventor: Ronald T. Smith, Irvine, CA (US)

(73) Assignee: Novartis AG, Basel (CH)

( * ) Notice: Subject to any disclaimer, the term of this patent is extended or adjusted under 35 U.S.C. 154(b) by 53 days.

(21) Appl. No.: 15/620,159

(22) Filed: Jun. 12, 2017

(65) Prior Publication Data

US 2017/0356608 A1 Dec. 14, 2017

Related U.S. Application Data

(60) Provisional application No. 62/349,434, filed on Jun. 13, 2016.

(51) Int. Cl.

| | |
|---|---|
| *A61B 1/06* | (2006.01) |
| *F21S 10/02* | (2006.01) |
| *H01S 3/08* | (2006.01) |
| *H01S 3/00* | (2006.01) |
| *A61B 90/30* | (2016.01) |

(Continued)

(52) U.S. Cl.
CPC ............ *F21S 10/026* (2013.01); *A61B 90/30* (2016.02); *F21V 9/40* (2018.02); *H01S 3/0078* (2013.01); *H01S 3/08086* (2013.01); *A61F 9/007* (2013.01); *H01S 3/0092* (2013.01)

(58) Field of Classification Search
CPC ... A61B 1/0646; A61B 1/0661; A61B 3/0008; A61B 3/12; A61B 3/135; A61B 3/14; A61B 3/13; A61B 1/06; G02B 26/008; G02B 26/023; G02B 27/149; G02B 27/144; G02B 27/145; G02B 27/1046; G02B 27/1006
See application file for complete search history.

(56) References Cited

U.S. PATENT DOCUMENTS

| | | | | |
|---|---|---|---|---|
| 4,878,113 A | * | 10/1989 | Nakamura | ........... A61B 1/0638 348/71 |
| 5,295,989 A | * | 3/1994 | Nakamura | ............. A61F 9/008 606/10 |

(Continued)

FOREIGN PATENT DOCUMENTS

WO     2005/006943 A2     1/2005

*Primary Examiner* — Eduardo C Robert
*Assistant Examiner* — Michelle C Eckman

(57) ABSTRACT

An ophthalmic illumination system includes a light source to emit a light beam and a filter comprising a clear region to transmit visible light in the visible spectrum and a first filtered region to transmit visible light in a first spectral range. The filter is arranged within the optical path of the beam. The system includes a plurality of chromaticity sensors to receive a portion of the light beam transmitted by the filter and output a signal indicating chromaticity of the received beam. The system also includes a processor to receive the signal indicating chromaticity, compare the indicated chromaticity to a target chromaticity stored in memory and, based on the comparison, adjust the chromaticity of the light beam transmitted by the filter by generating a signal to move the filter from a first position in which the light beam is incident upon only the clear region to a second position in which the light beam is partially incident on both the clear region and the first filtered region.

19 Claims, 17 Drawing Sheets

(51) Int. Cl.
*F21V 9/40* (2018.01)
*A61F 9/007* (2006.01)

(56) References Cited

U.S. PATENT DOCUMENTS

| | | | | |
|---|---|---|---|---|
| 5,299,053 | A * | 3/1994 | Kleinburg | G02B 21/06 |
| | | | | 351/201 |
| 5,430,476 | A * | 7/1995 | Hafele | A61B 1/042 |
| | | | | 348/270 |
| 5,832,159 | A * | 11/1998 | Davis | A61B 1/00117 |
| | | | | 385/53 |
| 5,982,974 | A * | 11/1999 | Davis | A61B 1/00117 |
| | | | | 362/551 |
| 6,061,591 | A * | 5/2000 | Freitag | A61B 5/0071 |
| | | | | 600/476 |
| 6,179,421 | B1 * | 1/2001 | Pang | A61B 3/12 |
| | | | | 351/205 |
| 6,271,920 | B1 * | 8/2001 | Macfarlane | G01J 3/52 |
| | | | | 356/243.5 |
| 6,309,070 | B1 * | 10/2001 | Svetliza | A61B 3/1225 |
| | | | | 351/221 |
| 7,654,716 | B1 * | 2/2010 | Bhadri | A61B 3/13 |
| | | | | 362/572 |
| 9,386,918 | B2 | 7/2016 | Ammari et al. | |
| 2001/0007494 | A1 * | 7/2001 | Takada | A61B 3/0008 |
| | | | | 351/221 |
| 2003/0035301 | A1 * | 2/2003 | Gardiner | A61N 5/0619 |
| | | | | 362/583 |
| 2006/0023272 | A1 * | 2/2006 | Tezuka | H04N 1/6033 |
| | | | | 358/518 |
| 2006/0268231 | A1 * | 11/2006 | Gil | A61B 3/12 |
| | | | | 351/221 |
| 2008/0079803 | A1 * | 4/2008 | Sekiguchi | A61B 1/0005 |
| | | | | 348/45 |
| 2009/0004126 | A1 * | 1/2009 | Lowndes | A61K 8/02 |
| | | | | 424/63 |
| 2009/0062662 | A1 * | 3/2009 | Zuluaga | A61B 1/00048 |
| | | | | 600/478 |
| 2009/0099460 | A1 * | 4/2009 | Zuluaga | A61B 1/00039 |
| | | | | 600/478 |
| 2009/0153798 | A1 * | 6/2009 | Dick | A61B 5/021 |
| | | | | 351/206 |
| 2009/0240138 | A1 | 9/2009 | Yi | |
| 2010/0261966 | A1 * | 10/2010 | Reimer | A61B 1/0646 |
| | | | | 600/160 |
| 2010/0296727 | A1 * | 11/2010 | Stern | G01N 21/6452 |
| | | | | 382/154 |
| 2011/0292344 | A1 * | 12/2011 | Papac | A61B 3/0008 |
| | | | | 351/221 |
| 2012/0083772 | A1 | 4/2012 | Rubinfeld et al. | |
| 2012/0203086 | A1 * | 8/2012 | Rorabaugh | A61B 3/1173 |
| | | | | 600/321 |
| 2013/0128223 | A1 * | 5/2013 | Wood | A61B 5/0077 |
| | | | | 351/206 |
| 2014/0055751 | A1 * | 2/2014 | Wang | G02B 27/22 |
| | | | | 353/7 |
| 2014/0347634 | A1 * | 11/2014 | Bommerbach | H04N 9/3158 |
| | | | | 353/31 |
| 2015/0042996 | A1 * | 2/2015 | Funamoto | G01J 3/50 |
| | | | | 356/402 |
| 2015/0354787 | A1 * | 12/2015 | Chang | H04N 9/00 |
| | | | | 362/84 |
| 2017/0293134 | A1 * | 10/2017 | Otterstrom | G02B 23/2461 |
| 2018/0051865 | A1 * | 2/2018 | Cui | F21V 9/30 |
| 2018/0173087 | A1 * | 6/2018 | Hsieh | G03B 21/2013 |
| 2018/0188640 | A1 * | 7/2018 | Huang | G03B 21/204 |

* cited by examiner

OPHTHALMIC ILLUMINATION SYSTEM WITH CONTROLLED CHROMATICITY

FIELD

This present disclosure relates generally to ophthalmic illuminators. More particularly, the present disclosure relates to devices, systems, and methods of controlling chromaticity of ophthalmic illumination systems.

BACKGROUND

Ophthalmic microsurgical procedures frequently require precision cutting and/or removing of various eye tissues. During such surgical procedures, proper illumination of the inside of the eye is important, and ophthalmic illumination systems are typically used to illuminate to the surgical field. A user, such as a surgeon or other medical professional, may insert an illumination probe into the eye to illuminate the inside of the eye for a procedure. Typically, the probe is connected to an optical port of an ophthalmic illumination system. The ophthalmic illumination system, which may be housed in a surgical console, includes a light source. The illumination system may also include other optical elements, such as collimating and condensing optics, that facilitate transmission of a light beam generated by the light source into an optical fiber extending into the probe.

During design and assembly of the ophthalmic illumination system, manufacturers seek to optimize various parameters and characteristics of the light beam, including chromaticity. Unfortunately, the chromaticity of a light beam generated by a light source, such as a supercontinuum laser engine, may not be initially calibrated as desired and tends to change with time. Such chromaticity shifts may adversely impact the surgeon's view of the surgical field, and could elevate the risk of phototoxicity in some cases. Accordingly, a need exists for improved illuminator systems that can accurately and efficiently configure, control, and maintain chromaticity over time.

SUMMARY

In general, the present disclosure relates to an ophthalmic illumination system that includes a light source configured to emit a light beam and a filter comprising a clear region configured to transmit visible light in the visible spectrum and a first filtered region configured to transmit visible light in a first spectral range, the filter arranged within the optical path of the light beam. The ophthalmic illumination system further includes a processor configured to adjust the chromaticity of the light beam transmitted by the filter by generating a signal to move the dichroic filter from a first position in which the light beam is incident upon only the clear region to a second position in which the light beam is partially incident on both the clear region and the first filtered region. In certain embodiments, the processor is configured to further adjust the chromaticity of the light beam transmitted by the dichroic filter by generating a signal to move the dichroic filter from the second position to a third position in which the light beam is partially incident on both the clear region and the first filtered region. In certain embodiments, the processor generates a signal to move the dichroic filter based on a measurement of time hours of the light source.

According to certain embodiments, an ophthalmic illumination system includes a supercontinuum laser configured to emit a white laser beam, and a first filter and a second filter arranged within the optical path of the white laser beam. The first filter comprises a first unfiltered region configured to transmit visible light in the visible spectrum, a first filtered region configured to transmit visible light in a first spectral range, and a second filtered region configured to transmit visible light in a second spectral range. The second filter comprises a second unfiltered region configured to transmit visible light in the visible spectrum, a third filtered region configured to transmit visible light in a third spectral range, and a fourth filtered region configured to transmit visible light in a fourth spectral range. The first filter and the second filter are independently moveable. The system further comprises a plurality of chromaticity sensors configured to receive a portion of the laser beam transmitted by the first and second filters and output a signal indicating a chromaticity value for the received portion of the beam. The system also includes a processor configured to receive the signals output by the plurality of chromaticity sensors, compare the indicated chromaticity values to one or more target chromaticity values stored in memory, and, based on the comparison, adjust the chromaticity of the light beam transmitted by the filters by generating a signal to move the first or second filter such that the laser beam is partially incident on an unfiltered region and a filtered region.

The first unfiltered region and the first filtered region may be separated by a distinct boundary. The distinct boundary may comprise a line nonperpendicular to a direction of motion of the first filter.

The first unfiltered region and the first filtered region may be separated by a gradient region which transitions from clear to the first filtered region, and the gradient region may be situated around a centerline extending nonperpendicular to a direction of motion of the first filter.

In certain embodiments, the filter is moved rotationally. Additionally or alternatively, the filter may be moved horizontally or vertically. The first spectral range may include wavelengths between 615 and 785 nm, or between 420 and 495 nm.

According to certain embodiments, an ophthalmic illumination system includes a light source configured to emit a light beam and a filter. The filter includes a clear region configured to transmit visible light in the visible spectrum and a first filtered region configured to transmit visible light in a first spectral range. The filter is arranged within the optical path of the light beam. The system also includes a plurality of chromaticity sensors, each configured to receive a portion of the light beam transmitted by the filter and output a signal indicating a chromaticity of the received portion of the light beam. The system further includes a processor configured to receive the signal indicating a chromaticity of the light beam from the chromaticity sensors, compare the indicated chromaticity of the light beam to a target chromaticity stored in memory, and based on the comparison, adjust the chromaticity of the light beam transmitted by the filter by generating a signal to move the filter from a first position in which the light beam is incident upon only the clear region to a second position in which the light beam is partially incident on both the clear region and the first filtered region. In certain embodiments, the signal indicating a chromaticity of the light beam output by each chromaticity sensor corresponds to the X-bar, Y-bar, or Z-bar tristimulus function.

In certain embodiments, the clear region and the first filtered region are separated by a distinct boundary. The distinct boundary may comprise a line nonperpendicular to a direction of motion of the dichroic filter.

In certain embodiments, the filter may be moved rotationally, horizontally, and/or vertically, and the light source may be a supercontinuum laser configured to emit a white laser beam. In certain embodiments, the first spectral range may include wavelengths between 615 and 785 nm, or between 420 and 495 nm.

In certain embodiments, the filter may further comprise a second filtered region configured to transmit visible light in a second spectral range. The system may also include a second filter comprising a clear region configured to transmit visible light in the visible spectrum and a second filtered region configured to transmit visible light in a second spectral range. The second filter may be arranged downstream of the first filter in the optical path of the light beam, and the processor may be further configured to adjust the chromaticity of the light beam transmitted by the first and second filters by generating a signal to move the second filter from a first position in which the light beam is incident upon only the clear region to a second position in which the light beam is partially incident on both the clear region and the second filtered region.

According to certain embodiments, an ophthalmic illumination system includes a light source configured to emit a light beam and a filter comprising a clear region configured to transmit visible light in the visible spectrum and a first filtered region configured to transmit visible light in a first spectral range. The filter is arranged within the optical path of the light beam. The system further includes a processor configured to track cumulative operating time of the light source and, based on the tracked cumulative operating time, adjust the chromaticity of the light beam transmitted by the filter by generating a signal to move the filter from a first position in which the light beam is incident upon only the clear region to a second position in which the light beam is partially incident on both the clear region and the first filtered region.

Certain embodiments of the present disclosure may provide one or more technical advantages. For example, embodiments of the present disclosure may provide an improved view of a surgical field by optimizing and maintaining the chromaticity of a light source. This can be particularly beneficial over the life of a supercontinuum laser engine, which tends to shift toward red or blue over time. Further, certain embodiments may reduce risk of phototoxicity induced by overexposure to blue light during retinal procedures.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1A:
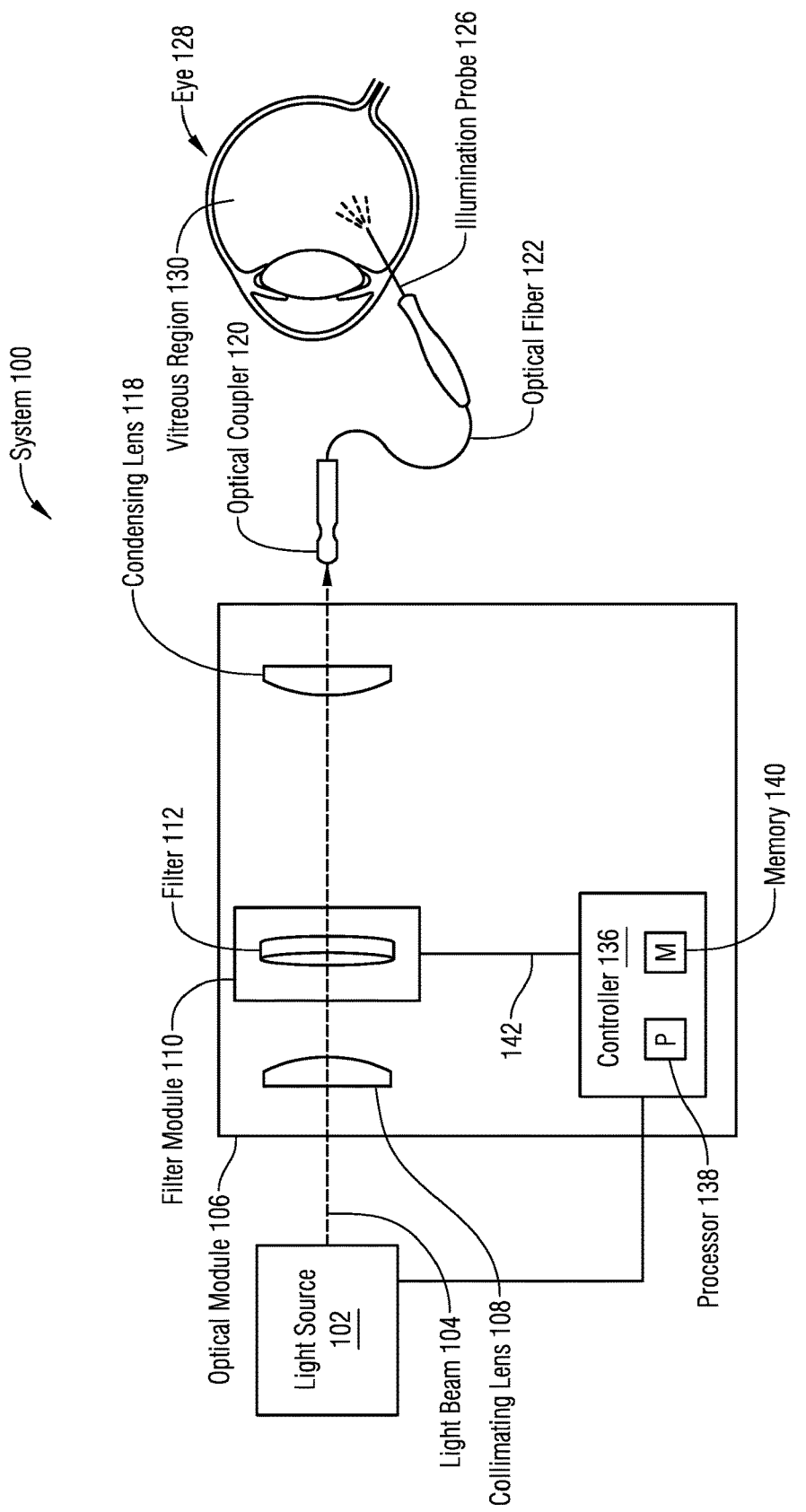
FIGS. 1A-1D illustrate ophthalmic illumination systems operable to control chromaticity of a light beam, according to certain embodiments.

One skilled in the art will appreciate that the drawings, described below, are for illustration purposes only and do not limit the scope of the disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. Further, in some instances the same reference numbers are used throughout the drawings to refer to the same or like parts.

In general, the present disclosure relates to illumination systems for ophthalmic surgery, including vitrectomies. FIGS. 1A-1D illustrate examples of an illumination system 100 operable to control the chromaticity of a light source, according to certain embodiments.

In particular, system 100 of FIG. 1A includes a light source 102 (e.g., a supercontinuum laser engine) operable to direct a light beam 104 (e.g., a supercontinuum white laser beam) toward an optical module 106. Optical module 106 includes one or more collimating lenses 108, a filter module 110, and one or more condensing lenses 118 that are optically aligned to transmit light beam 104 toward optical coupler 120. Filter module 110 includes at least one filter 112, as well as electrical and/or mechanical components (not shown) to actuate or reposition the at least one filter 112. Optical module 106 further includes a controller 136, which includes a processor 138 and memory 140 configured to control components of filter module 110 so as to adjust the position of the at least one filter 112 and thereby modify or maintain the chromaticity of light beam 104 exiting optical module 106. Although filter module 110 is shown positioned between collimating lens 108 and condensing lens 118 in this example, filter module 110 may be arranged in any suitable location of system 100.

Light source 102 may comprise a laser engine for generating light at a particular luminous flux and chromaticity. In certain embodiments, light source 102 is a supercontinuum laser engine. Other embodiments may use different types of lasers, including but not limited to gas lasers, dye lasers, metal vapor lasers, solid state lasers, semiconductor lasers, and fiber lasers. Light source 102 may be any suitable light source for ophthalmic surgical illumination, including but not limited to a halogen tungsten lamp, high pressure arc lamp, or LED, for example.

Light beam 104 may be emitted from light source 102 over a relatively wide or narrow spectral range depending on the type of light source employed. In certain embodiments, light beam 104 is a white supercontinuum laser beam emitted at a calibrated chromaticity. Light source 102 may be calibrated at the time of manufacture to emit light beam 104 at a target chromaticity. If the chromaticity of light beam 104 is not initially calibrated as desired, the chromaticity may be set to a target chromaticity using one or more filters of the ophthalmic illumination system disclosed herein. In certain embodiments, the target chromaticity is white or substantially achromatic. In other embodiments, the target chromaticity may correspond to a particular color.

Components of optical module 106 are configured to transmit light beam 104 and, if necessary adjust the chromaticity of light beam 104 before it is directed into eye 128. In particular collimating lens 108 receives light beam 104 emitted from light source 102, and refracts the light to generally collimate light beam 104. Collimating lens 108 may be an achromatic lens to collimate light. Collimating lens 108 may comprise any suitable optical components for collimating light beam 104.

Filter module 110 comprises at least one filter 112, as well as components configured to control the position of filter 112. In certain examples, filter module 110 comprises one or more movement mechanisms, such as a brushless or brushed DC motor, stepper motor, servomotor, piezo actuator, hydraulic actuator, pneumatic actuator, electric actuator, or other actuator, coupled to filter 112 configured to adjust the spatial position of filter 112 (or portions thereof) with respect to light beam 104. Filter module 114 is communicatively coupled to controller 136, and may adjust the position of filter 112 in response to electronic signals received from controller 136.

Controller 136 may be communicatively coupled to filter module 110 and light source 102 via a wired or wireless connection 142. Controller 136 may include any suitable combination of hardware, firmware, and software. In particular, processor 138 may include one or more microprocessors, field-programmable gate arrays (FPGAs), controllers, or any other suitable computing devices or resources. Processor 138 may work, either alone or with other components depicted in FIG. 1, to provide the functionality described in the present disclosure. Memory 140 may take the form of volatile or non-volatile memory including, without limitation, magnetic media, optical media, random access memory (RAM), read-only memory (ROM), removable media, or any other suitable memory component. Memory 140 may store instructions for programs and algorithms that, when executed by processor 138, implement the functionality of controller 136 described in the present disclosure. Among other things, controller 136 may be programmed to (or may store software in memory 140 that, when executed by processor 138, is operable to) adjust the chromaticity of light source 102 by changing the position of filter 112, as described herein. For example, controller 136 may be programmed to (or may store software in memory 140 that, when executed by processor 138, is operable to) control one or more step motors, servomotors, or actuators coupled to filters 112 and/or 114 in order to control the spatial position of filters 112 and/or 114 with respect to light beam 104, and thereby adjust the chromaticity of light beam 104.

Figure 13:
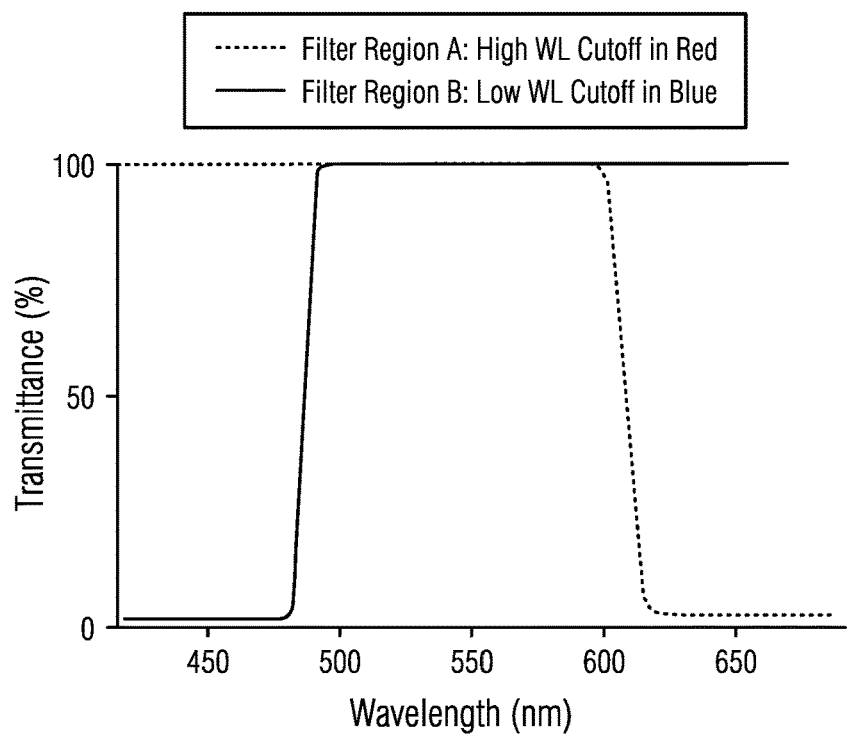
FIGS. 13-14 illustrate spectral characteristics of different filter regions, according to certain embodiments.
Figure 14:
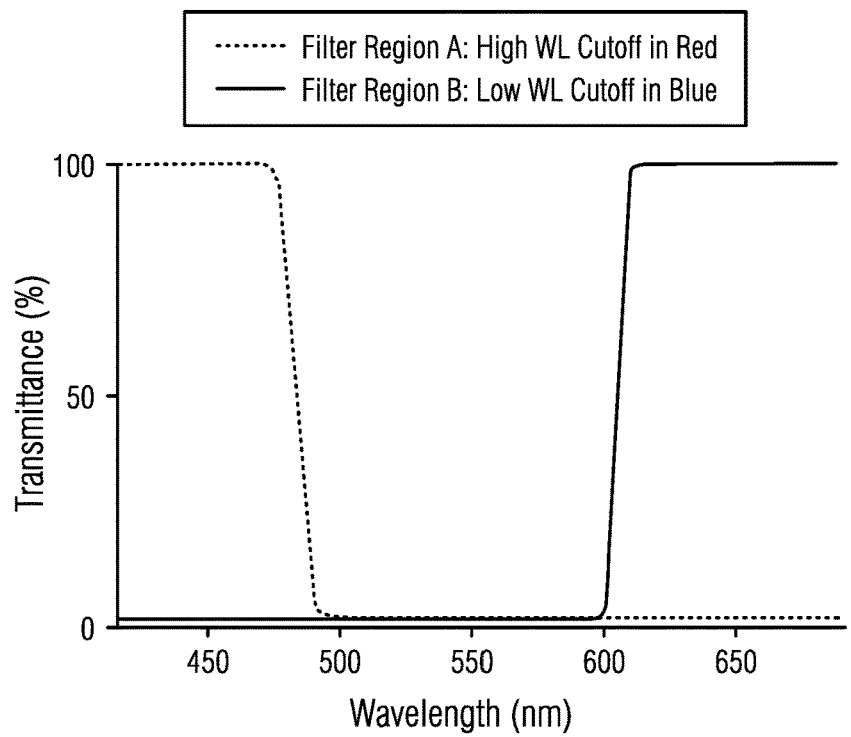

Filter 112 and/or 114 may be made of any suitable material (e.g., glass) in any appropriate shape or size (e.g., round, square, etc.) for transmission of light beam 104, as described herein. In certain embodiments, filter 112 and/or 114 is a dichroic filter comprising two or more regions having different spectral characteristics. For example, particular regions of filter 112 and/or 114 may comprise low- or high-wavelength cutoff filters in various zones of the visible spectrum. Spectral characteristics of example filter regions are illustrated in FIGS. 13 and 14. For instance, in certain embodiments, filters 112 and/or 114 may comprise a dichroic filter with a clear region to transmit substantially all light in the visible spectrum, a low-wavelength cutoff region in which spectral transmittance below the cutoff (e.g., 495 nm) is near 0% and above the cutoff is near 100%, and/or a high-wavelength cutoff region in which spectral transmittance below the cutoff (e.g., 615 nm) is near 100% and above the cutoff is near 100% (see, e.g., FIG. 13). Additionally, in certain embodiments, filter 112 may comprise a dichroic filter with a first clear region, a region that is colored (e.g., red) to transmit visible light only above or within a particular spectral range (e.g., 615-785 nm), and/or a region colored (e.g., blue) to transmit visible light only below or within another spectral range (e.g., 420-495 nm) (see, e.g., FIG. 14).

It should be noted that the spectral characteristics depicted in FIGS. 13 and 14 are idealized, and the filter regions used in real-world embodiments will include imperfections typical in the state of the art. Further, various embodiments of filter 112 may include any suitable number and combination of filter regions with different spectral filtering characteristics to adjust, maintain, and optimize chromaticity of a light beam. Additionally, various embodiments (such as those depicted in FIGS. 1B, 1C, and 1D) include multiple filters configured to adjust the chromaticity of a light beam in a complementary and/or additive manner. Examples of different designs for filters 112 and/or 114 are illustrated in FIGS. 3-9 and discussed in additional detail below, though one skilled in the art will recognize that numerous additional configurations are within the scope of the present disclosure. Various filter implementations are described in U.S. application Ser. No. 14/309,653 (Pub. No. 2015/0366446A1), filed Jun. 19, 2014, which is incorporated by reference herein in its entirety.

Condensing lens 118 of is configured to focus light beam 104 into optical coupler 120. Condensing lens 118 may comprise any suitable optical components for focusing light beam 104 for transmission through optical coupler 120 and optical fiber 122.

Optical coupler 120 receives light beam 104 from condensing lens 118 and transmits light beam 104 through an optical fiber 122 and illumination probe 126, where light beam 104 illuminates eye 128, such as a vitreous region 130. Optical coupler 120 couples optical module 106 to optical fiber 122 such that light beam 104 may be focused and directed into optical fiber 122. Optical coupler 120 may include any suitable components to align optical module 106 with optical fiber 122 to facilitate transmission of light beam 104. In certain embodiments, optical module 106 is housed within a surgical console comprising attachment points (not shown) suitable for removably connecting to optical coupler 120.

Optical fiber 122 may include a flexible configuration to allow generally unimpeded manipulation of illumination probe 126. Optical fiber 122 may include an optically transmissive fiber optic core surrounded by a cladding material having a generally low index of refraction relative to the fiber optic core. The fiber optic core may be made of various materials, including but not limited to, glass and plastics. Optical fiber 122 may also include additional layers depending on the requirements of a particular application. For example, optical fiber 122 may include a buffer material encasing cladding material, as well as an outer protective jacket (such as a plastic or metal tube) for shielding the cable's interior components from damage. Optical fiber 122 may comprise a multimode fiber.

In certain embodiments, a supercontinuum laser beam 104 emitted by light source 102 possesses a high degree of spatial coherence, enabling beam 104 to be focused to small spot sizes for delivery to optical fiber 122. In such embodiments, optical fiber 122 may be a nano-scaled fiber optic cable. Nano-scale optic fibers generally have a diameter (or other largest cross-sectional dimension) of less than 100 microns. When employed as fiber optic core of optical fiber 122 and illumination probe 126, the small diameter of nano-scale optic fiber may enable a reduction in the cross-sectional area of probe 126, which in turn may reduce the size of the surgical incision in sclera eye 128 through which probe 126 is inserted. Depending on the size of optical fiber 122, the incision may be small enough to render the resulting wound substantially self-healing, thereby eliminating the need to employ additional procedures to close the incision, such as sutures. Additionally, due to the small size of nano-scale optic fibers, it may be possible to integrate illumination probe 126 with another surgical instrument, such as an infusion cannula (not shown), to reduce the number of surgical incision required for inserting surgical instruments during a vitreoretinal procedure.

Optical fiber 122 extends to and through illumination probe 126 to transmit light beam 104 into eye 128. Probe 126 comprises a hand piece held by the surgeon to allow manipulation of probe 126 in eye 128. As shown in FIG. 1, probe 126 may be inserted in eye 128 through an incision in the pars plana region, and may be positioned to illuminate the inside or vitreous region 130 of eye 128 during an ophthalmic surgical procedure. Light beam 104 carried by optical fiber 122 through illumination probe 126 is back-scattered against interior surfaces of eye 128, illuminating the surgical site.

As noted above, in certain embodiments, light beam 104 is a white supercontinuum laser beam emitted at a pre-calibrated chromaticity. White light is often desirable for illuminating biological materials, including the eye, during surgery. Filament or gas discharge lamps, as well as LEDs, are often used to generate a white light beam in an ophthalmic illumination system, but the power and quality of the beam produced by such devices is inadequate for certain applications. And, while lasers provide very high quality light beams, they are typically confined to a very narrow spectral range. Supercontinuum lasers, however, are capable of producing a generally broadband light over a relatively wide spectral range. Supercontinuum lasers may operate by passing a generally narrow bandwidth pulsed pump beam through a dispersive, non-linear medium, such as a photonic crystal fiber. As the pump beam propagates through the dispersive, non-linear medium, a series of non-linear processes act upon the pump beam to cause spectral broadening of the initial pump beam. The result is a spectral continuum extending across the visible spectrum.

The color of a light source 102, such as a supercontinuum laser engine, will at any given time have a measurable chromaticity value. The human eye has three different types of color-sensitive cone receptors, and the response of the eye to color may be described in terms of three tristimulus values (denoted X, Y, and Z) defined by the International Commission on Illumination (CIE) color space published in 1931, normalized according to the following equations:

$$x = \frac{X}{X+Y+Z}$$
$$y = \frac{Y}{X+Y+Z}$$
$$z = \frac{Z}{X+Y+Z} = 1 - x - y$$

Figure 12:
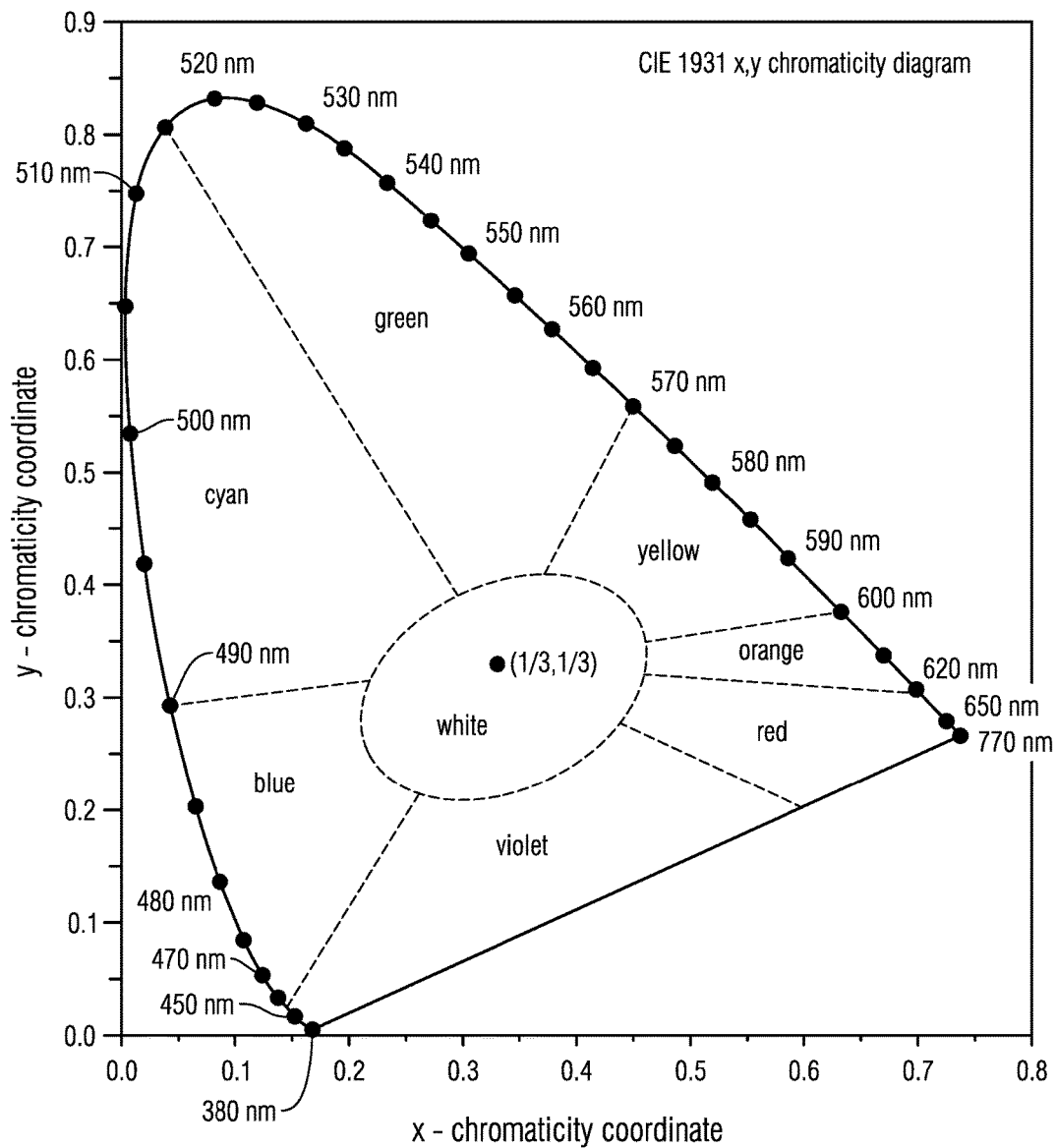
FIG. 12 illustrates a chromaticity diagram.

Accordingly, a complete diagram of all visible colors is three-dimensional. However, as a practical matter, the concept of color can be divided into two parts brightness and chromaticity. Accordingly, the CIE defined a derivative color space specified by x, y, and Y, known as the CIE xyY color space. This scheme can be used to characterize and plot perceived colors in a two-dimensional (x,y) space known as chromaticity. FIG. 12 depicts a chromaticity diagram in accordance with this approach. The outer curved boundary of the chromaticity diagram shown in FIG. 12 represents monochromatic light—the pure hues of a single wavelength, measured in nanometers. Colors at the curved boundary of the diagram are saturated. As one moves from the curved boundary toward the center of the figure, saturation decreases. The center of the figure corresponds to white light, which becomes fully achromatic at the coordinate x=y=1/3.

As noted above, the chromaticity of a supercontinuum laser beam 102 may be precisely calibrated at the time of manufacture to have a target chromaticity value (or range of values) within the white region of FIG. 12. At times, however, the chromaticity of a light beam emitted from a supercontinuum laser engine may not be exactly as desired at the time an ophthalmic illumination system is assembled. Moreover, due to changes in the laser engine that occur with time and use, the chromaticity of beam 102 may gradually change, typically shifting either redder (generally toward the right of FIG. 12) or bluer (generally toward the left side of FIG. 12). As the supercontinuum laser beam changes chromaticity, it will follow a particular trajectory (not necessarily a straight line) on the chromaticity diagram of FIG. 12 that depends on the individual characteristics of light source 102. Such chromaticity shifts may be undesirable as they risk impeding or obfuscating the surgeon's view of tissues in eye 128. Moreover, photo-toxicity damage to the retina may result from exposure to blue light.

Accordingly, certain embodiments of system 100 therefore include one or more filters that may be adjustably positioned to set or maintain the chromaticity of laser beam 102 at a target value or within a target range. Because white light may be generated by mixing colors on opposite sides of a white region of FIG. 12, the chromaticity of beam 104 which has shifted red, blue, or elsewhere on the chromaticity diagram of FIG. 12, may be adjusted (e.g., by controller 136) back to white by passing beam 104 through one or more spectral filters 112 configured to pass or block wavelengths in a particular spectral range. As beam 102 passes through a spectral filter 112, its chromaticity will change depending on the spectral transmission characteristics of filter 112.

In order to achieve finely-tuned chromaticity adjustments, certain embodiments of system 100 utilize one or more specialized dichroic filters 112 in which a spectral transmittance characteristic of varies in different regions. For example, optical module 106 may include a dichroic spectral filter 112 with two regions: a clear region that has no filter (e.g., bare glass or AR-coated glass) and a colored/filtered region that has a high- or low-wavelength cutoff (where transmittance of wavelengths on one side of the cutoff is near 100% and transmittance on the other side is ear 0%). Other embodiments may include a dichroic spectral filter 112 with three regions, such as a clear region that has no filter, a first colored/filtered region that has a first high- or low-wavelength cutoff zone, and a second colored/filtered region that has a second high- or low-wavelength cutoff zone. Additional embodiments may include additional regions and color variations.

For example, the chromaticity of a white laser beam 104 which has become redder over time (shifted to the right of FIG. 12, out of the white zone) may be restored to white by passing it through a region of dichroic filter 112 that removes light within the red wavelength spectrum (e.g., a short pass filter with a cutoff wavelength in or near the red spectrum—approximately 615-785 nm), or adds light within the blue wavelength spectrum (e.g., a short pass filter region with a cutoff wavelength in or near the blue spectrum—approximately 420-495 nm). Similarly, the chromaticity of a white laser beam 104 which has become bluer over time (shifted to the left of FIG. 12, out of the white zone) may be restored to white by passing it through a region of dichroic filter 112 that removes light within the blue wavelength spectrum (e.g., a long pass filter region with a cutoff wavelength in or near the blue spectrum) or adds light within the red wavelength spectrum (e.g., a long pass filter region with a cutoff wavelength in or near the red spectrum).

In certain embodiments, a boundary between different regions in the filter may be a distinct demarcation between homogenous regions (e.g., sharply-defined lines). For example, in the case of a three-zone embodiment of filter 112 that includes a clear region that has no filter, a first filter region having a high wavelength cutoff zone near 615 nm, and a second filter region having low-wavelength cutoff zone near 495 nm (see, e.g., FIG. 13), transmittance of a supercontinuum laser beam 102 that passes entirely through the clear region will be unaltered. If transmitted entirely through the first filter region, transmittance of the beam above the high-wavelength cutoff zone will approach 0%, and below the high-wavelength cutoff zone will approach 100%. Similarly, if transmitted entirely through the second filter region, transmittance of the beam above the low-wavelength cutoff zone will approach 100%, and below the high-wavelength cutoff zone will approach 0%.

However, if a boundary line between the first and second regions of the filter is within the cross-sectional area of the supercontinuum laser beam, the beam transmittance above the cutoff will be neither 0% nor 100%, but an intermediate value that depends on the fraction of the beam passing through the respective regions. Similarly, if a boundary line between the first and third regions of the filter is within the cross-sectional area of the supercontinuum laser beam, the beam transmittance below the cutoff will be neither 0% nor 100%, but an intermediate value that depends on the fraction of the beam passing through the respective regions. Therefore, according to particular embodiments of system 100, moving or repositioning filters 112 and/or 114 (e.g., rotating or shifting a filter wheel to change the location of a region boundary with respect to the impinging laser beam) can be used to achieve incremental or continuous adjustments to the transmittance characteristics and chromaticity of beam 104.

Figure 3:
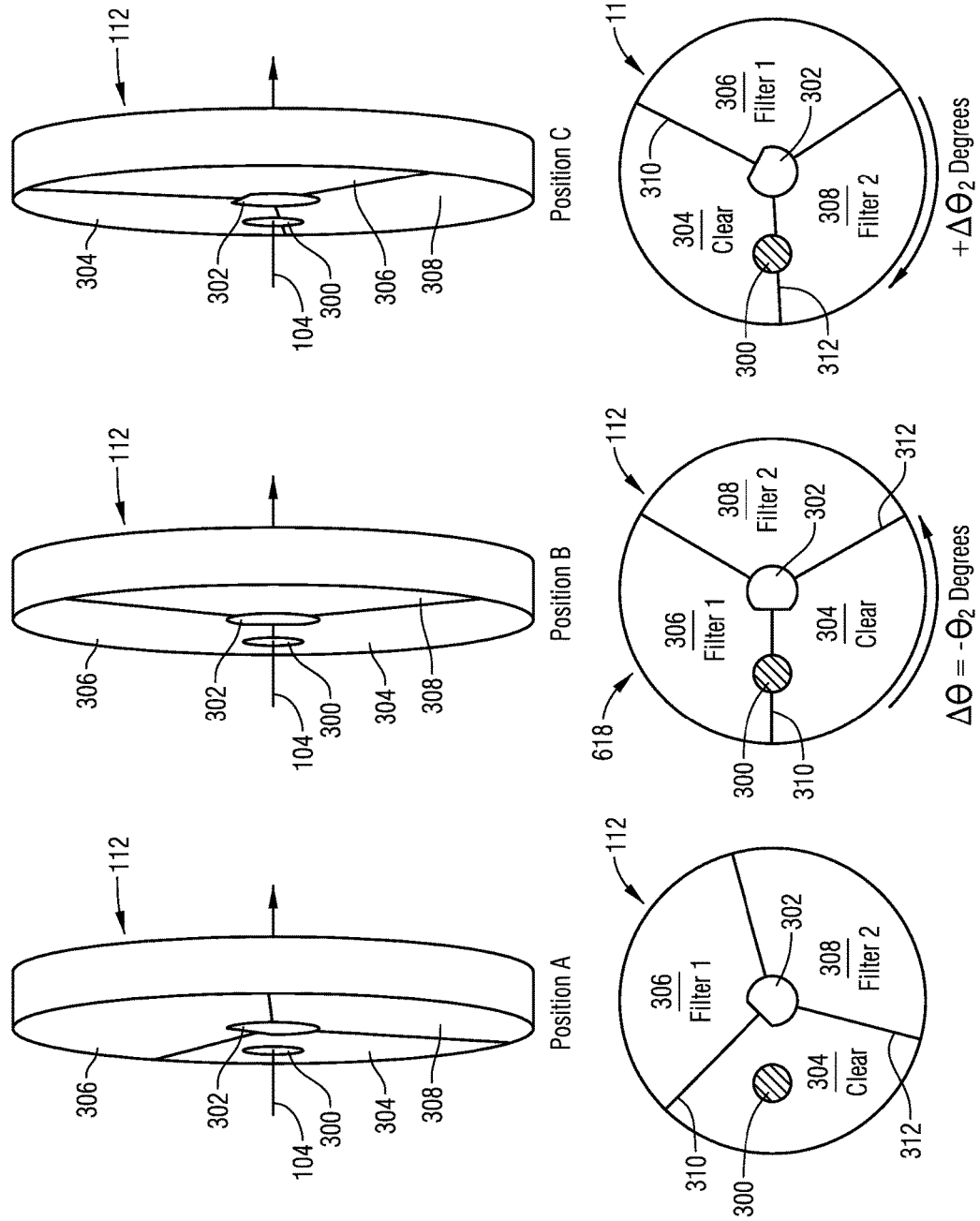
FIGS. 3, 4A, and 4B illustrate use of a filter to control chromaticity of a light beam, according to certain embodiments.

For example, FIG. 3 illustrates how one example of filter 112 may be moved to adjust chromaticity of beam 104. Here, filter 112 is arranged perpendicular to the optical path of light beam 104, and the lateral and vertical position of light beam 104 and filter 112 are fixed. Light beam 104 impinges on filter 112 at point 300; thus, point 300 corresponds to a cross-section of light beam 104. Further, filter 112 is configured to rotate about a center axis by means of a mechanical axle arranged in orifice 302, under the control of controller 136. Filter 112 includes regions 304, 306, and 308, which may be any suitable color or include any suitable spectral filtering characteristics.

In position A (on the left), point 300 lies within region 304, which in this example is clear. Accordingly, in position A, the chromaticity of light beam 104 is unchanged as it passes through filter 112.

In position B, filter 112 has been rotated counter-clockwise from position A ($\Delta\Theta=-\Theta_1$ degrees), such that impingement point 300 now lies on boundary 310 separating clear region 304 from filter region 306. As a result, the chromaticity of light beam 104 will be adjusted in proportion to the fraction of point 300 that passes through region 306. Assuming, for example, that region 306 comprises a low wavelength cutoff in blue, the chromaticity of light beam 104 will shift toward the right on FIG. 12 (redder) as filter 112 moves from position A to position B. Thus, the chromaticity of a white laser beam 104 which has become bluer over time (shifted to the left of FIG. 12, out of the white zone) may, in some embodiments, be restored to white by passing it through a dichroic filter 112 that adds light above the blue wavelength spectrum (including red), as shown in FIG. 3B.

In position C, filter 112 is rotated clockwise from position A ($\Delta\Theta=+\Theta_2$ degrees), such that impingement point 300 lies on boundary 312 separating clear region 304 from region 308. Assuming in this example that region 308 comprises a high wavelength cutoff in red, the chromaticity of light beam 104 will shift to the left on FIG. 12 (bluer) as filter 112 moves from position A to position C. Thus, the chromaticity of a white laser beam 104 which has become redder over time (shifted to the right of FIG. 12, out of the white zone) may, in some embodiments, be restored to white by passing it through a dichroic filter 112 that adds light below the red wavelength spectrum (including blue), as shown in FIG. 3C. In various embodiments, the regions of filter 112 may comprise any suitable color or have any suitable spectral filtering characteristics.

Further, in certain embodiments, controller 136 may be configured to generate a signal to incrementally or continuously adjust filter 112 relative to beam 104, in order to incrementally change the fraction of beam 104 passing through each region (and thus the chromaticity of beam 104). For example, beginning at position B in FIG. 3, rotating filter 112 clockwise 1° would result in a smaller fraction of point 300 passing through filter region 306—reducing the chromaticity adjustment of beam 104—but rotating filter 112 counter-clockwise 1° would result in a larger fraction of point 300 passing through filter region 306—increasing the chromaticity adjustment of beam 104. Analogously, beginning from position C in FIG. 3, rotating filter 112 clockwise 1° would increase the fractional area of point 300 in region 308, while rotating filter 112 counter-clockwise 1° would decrease the fractional area, thereby increasing or decreasing the chromaticity adjustment of beam 104, respectively.

Figure 4A:
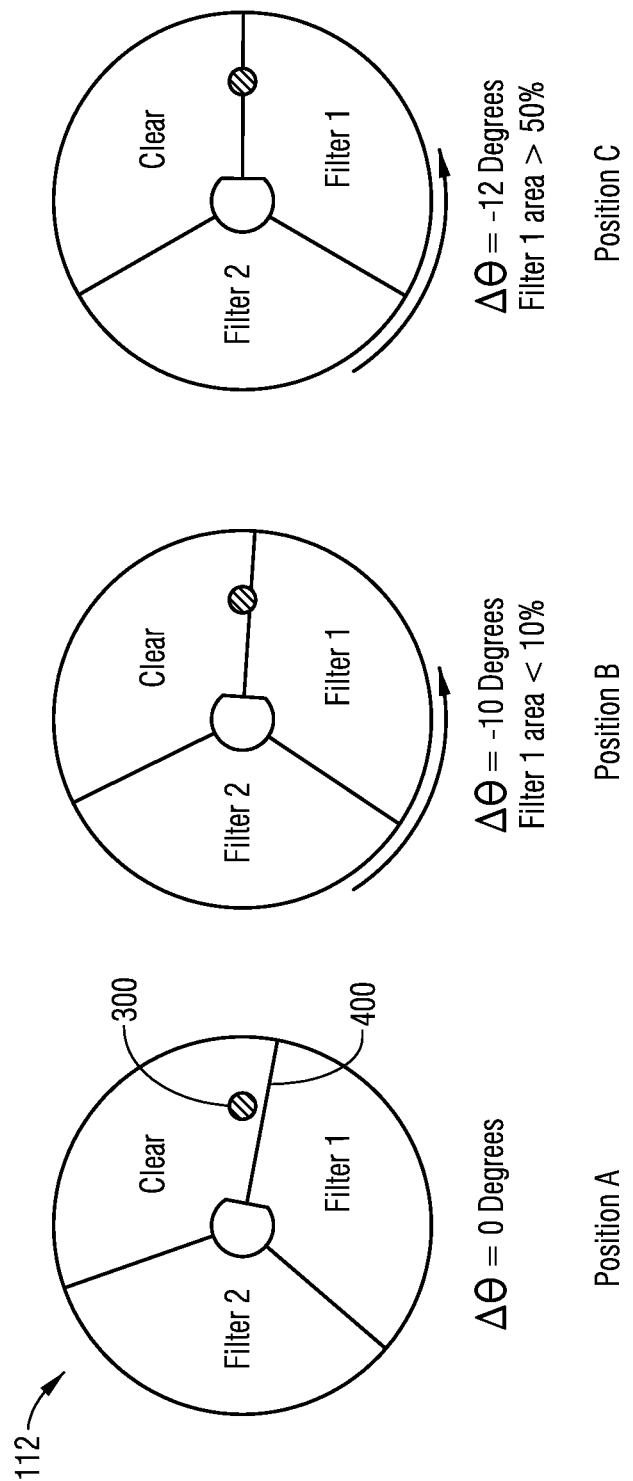
Figure 4B:
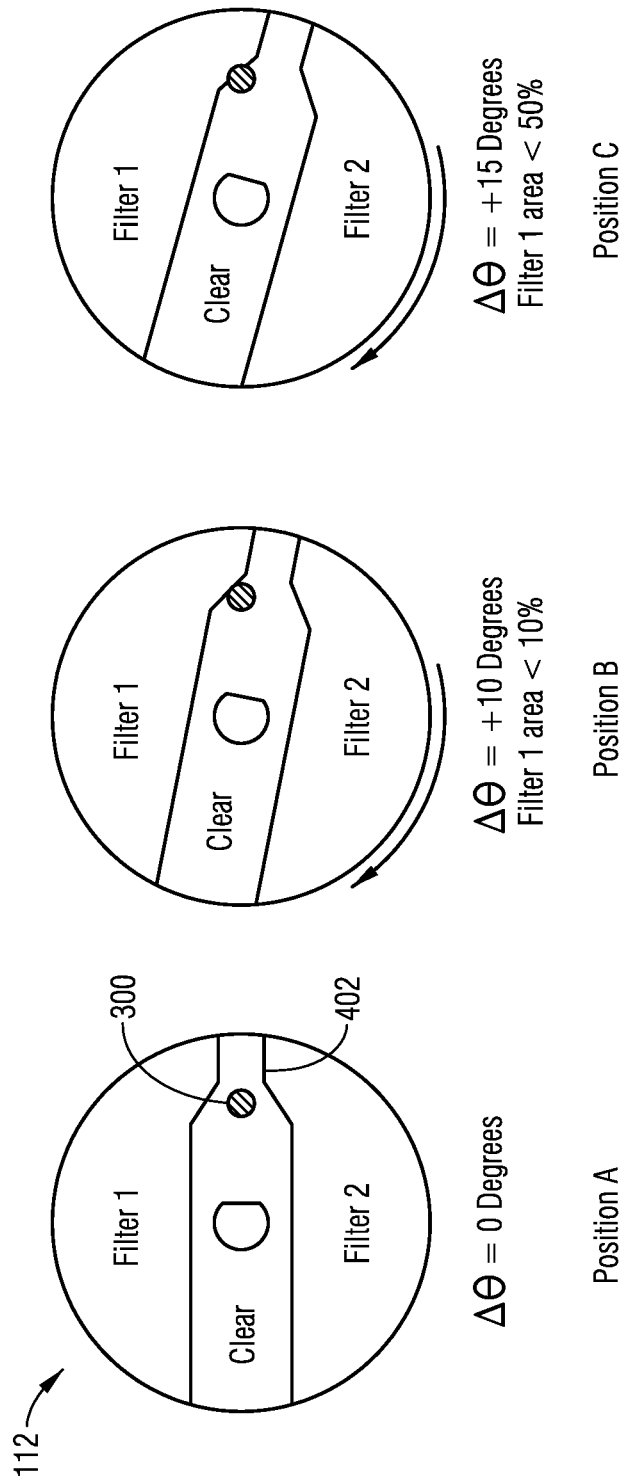

Incremental adjustment of chromaticity is further illustrated in the examples of FIGS. 4A and 4B, which depict how example filter 112 may be incrementally moved (in this instance, rotated) relative to an impingement point 300 of light beam 104 to enable fine chromaticity adjustments. Beginning with FIG. 7A, filter 112 is arranged at position A (ΔΘ=0°) in which point 300 lies entirely within a clear region of filter 112. Accordingly, the chromaticity of the light beam does not change as it passes through filter 112 in position A. At position B, filter 112 is rotated approximately 10° counterclockwise from position A (ΔΘ=−10°), where point 300 slightly impinges on boundary 400. Accordingly, a small fraction of point 300 passes through the first filter region, while the majority passes through the clear region. As a result, the chromaticity of the light beam 104 is slightly adjusted with respect to position A (e.g., slightly redder or bluer, based on the spectral filtering characteristics of the first filter region). At position C, filter 112 is rotated approximately 2° further counterclockwise from position B (ΔΘ=−12° with respect to position A). At position C, point 300 still impinges on boundary 400, but a larger fraction of point 300 passes through the first filter region, while the rest passes through the clear region. As a result, the chromaticity of the light beam 104 is further adjusted (e.g., more red or more blue, with respect to position B).

Turning to FIG. 4B, filter 112 is arranged at position A (ΔΘ=0°) in which point 702 lies entirely within a clear region of filter 112. Accordingly, the chromaticity of the light beam 104 does not change as it passes through filter 112 in position A. At position B, filter 112 is rotated approximately 10° clockwise (ΔΘ=+10°) from position A, where point 300 impinges on boundary 402. Accordingly, a small fraction of point 300 passes through the first filter region, while the majority passes through the clear region. As a result, the chromaticity of the light beam 104 is adjusted with respect to position A (e.g., redder or bluer, based on the spectral filtering characteristics of the first filter region). Similarly, at position C, filter 112 is rotated approximately 5° further in the clockwise direction from position B (4Θ=+15° with respect to position A). At position C, point 300 still impinges on boundary 402, but a larger fraction of point 300 passes through the first filter region, while the rest passes through the clear region. As a result, the chromaticity of the light beam 104 is further adjusted (e.g., more red or more blue, as the case may be).

Although not drawn to scale, FIGS. 4A and 4B also illustrate that additional chromaticity control may be realized by modifying on the angle of a region boundary with respect to the movement of filter 112. In certain instances where a boundary line between regions runs approximately perpendicular to a direction of motion of a filter 112, a high resolution motor or actuator (e.g., a stepper motor or servomotor configured to adjust the position of filter 112 in very small increments) may be required to adjust chromaticity with requisite precision. Reducing the angle between the boundary line and the direction of motion below 90 degrees, however, may reduce the motion of the boundary line across the beam given a fixed resolution/step size. If, for example, the angle between the boundary line and the direction of motion is 45 degrees, the motion of the boundary line cross the beam is only 70.7% of the motion at 90 degrees. Accordingly, certain embodiments include one or more dichroic filters 112 configured such that the angle between a boundary line between regions and a direction of motion is below 90 degrees (e.g., between 30 and 60 degrees), to facilitate more granular adjustments to chromaticity.

FIGS. 4A and B illustrate that the impact of one degree of rotation on the fractional impingement of point 300 at boundaries 400 and 402 is not equal, but rather depends on the design of the boundaries. Hence, a two-degree rotation of filter 112 in FIG. 4A (from position B to C) may increase the area of point 300 impinging on the Filter 1 (first filter) region from approximately 10% to approximately 50%, while a five-degree rotation of filter 112 in 4B (from position B to C) may increase the area of point 300 impinging on the Filter 1 region from approximately 10% to approximately 50%. That is, though the adjustment from position B to C in FIG. 4B is 2.5× greater than the adjustment from position B to C in FIG. 4A, it may yield a comparable change in the fractional impingement area of beam 104, and thus a finer adjustment to chromaticity. Thus, the particular design of the boundary between regions may act as a multiplier to increase or decrease the impact of a fixed movement on the chromaticity of light beam 104. Accordingly, filter designs such as those shown in FIG. 4B and elsewhere in the present disclosure may facilitate more granular chromaticity adjustments, despite limited resolution in a motor or actuator used to rotate or otherwise move filter 112. Accordingly, certain embodiments include one or more dichroic filters 112 that include an acute angle between a regional boundary line and a direction of motion.

Certain embodiments of system 100 may increase control over chromaticity by varying other aspects of filter 112. For example, rather than using a filter 112 in which the boundaries between regions are distinct, certain embodiments include one or more filters 112 in which a cutoff wavelength or transmission curve varies incrementally or continuously across a gradient zone or area separating different regions. In such embodiments, incremental movements of filter 112 (e.g., rotating or shifting a filter wheel to change the location of a region boundary with respect to the impinging laser beam) may yield adjustments to the transmittance characteristics and chromaticity of the beam in smaller increments than would be possible using a filter design with distinct boundaries between regions.

FIGS. 5-8 illustrate example variations of filter 112 that may be used with embodiments of system 100. It is noted at the outset that the shapes, sizes, distances, and angles in these examples are not drawn to scale, nor are they limiting. Moreover, although particular filter colors or characteristics may be shown and discussed in FIGS. 5-8, the disclosure contemplates that any suitable filter types may be used. One skilled in the art will appreciate that many additional variations of the examples shown may lie within the scope of the disclosure.

Figure 5:
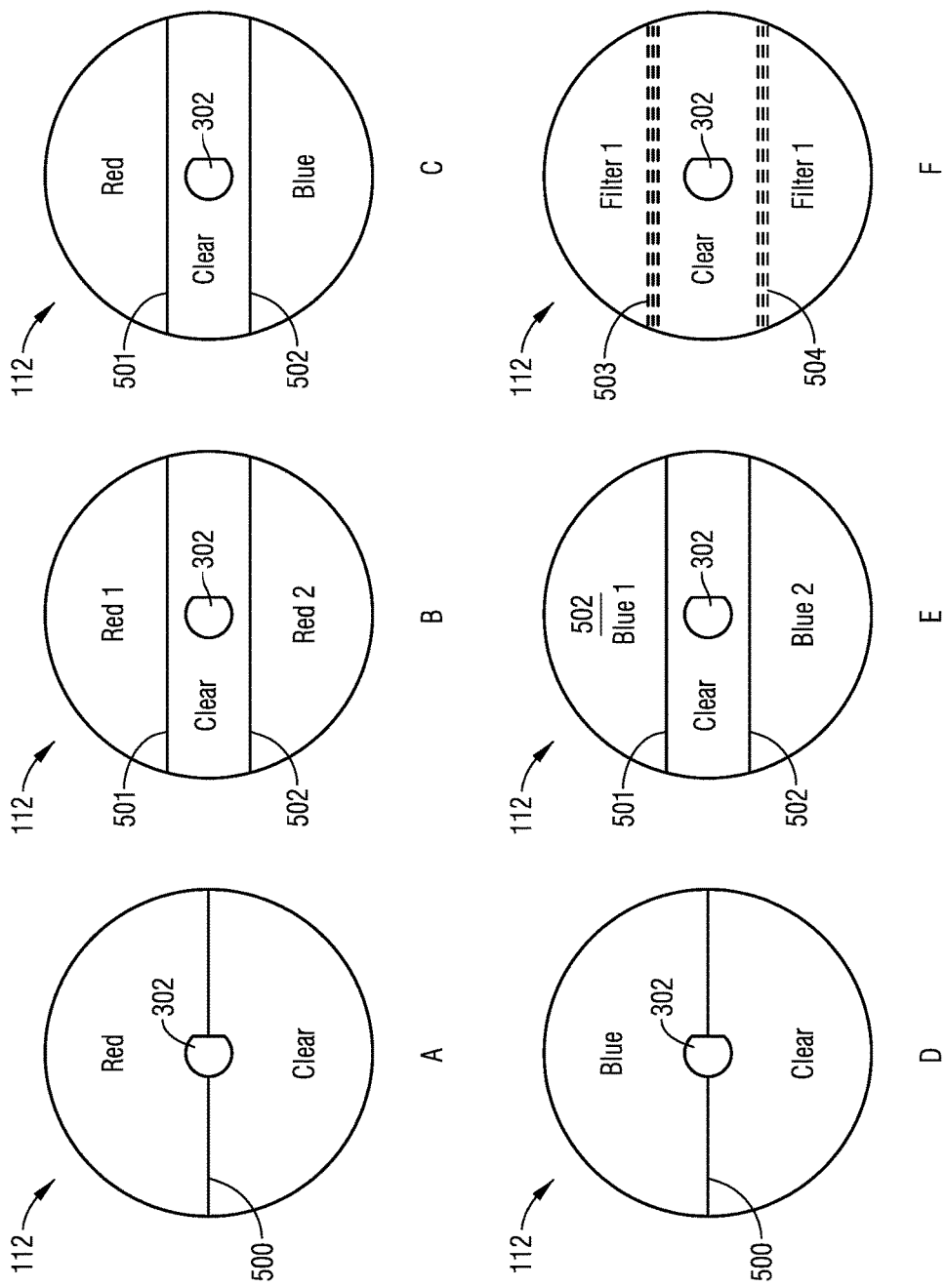
FIGS. 5-8 illustrate various filter designs, according to certain embodiments.

FIG. 5 illustrates several examples of a filter wheel 112. In 5A, filter 112 comprises a clear region and a red region separated by a distinct boundary 500. The red region may comprise a low wavelength cutoff in the red spectrum. In other embodiments, the red region may comprise a low wavelength cutoff between the blue and red spectrum, or in the blue spectrum. Filter 112 includes an orifice 302, which may be round, semicircular, or any other suitable shape, to facilitate rotational movement via a mechanical axle arranged in orifice 302. In 5A, the first region transmits at least a portion of light in the visible spectrum corresponding to red, which may include wavelengths in the range of approximately 615 nm to 785 nm. The second region is clear, and thus transmits the entire visible spectrum. As explained above, the chromaticity of light beam 104 may be modified by changing the position of filter 112 relative to the beam 104, such that the beam, or fractions of the beam, passes through each region (by impinging on the filter at the well-defined boundary between regions). This example would be useful to shift the chromaticity of a light beam toward the right size of FIG. 12 (toward red), to compensate for blue-shift of a supercontinuum white laser beam.

Example 5B illustrates a different configuration of filter 112 that includes a first, second, and third region separated by distinct boundaries 501 and 502. Although boundaries 501 and 502 are parallel, the disclosure contemplates that boundaries between filter regions may be otherwise arranged. In this example, the upper region and lower region transmit different portions of the visible spectrum that includes red, while the center region is clear. For example, the upper region may comprise a low-wavelength cutoff at approximately 615 nm, and the lower region may comprise a low-wavelength cutoff between 495 and 615 nm. By providing two regions that transmit different spectral ranges that include red but exclude blue, example 5B may facilitate more precise adjustments to the chromaticity of light beam 104. That is, the position of filter 112 may be adjusted such that a fraction of the light beam impinges on clear region 304 in combination with either the upper region or the lower region, depending on the particular chromaticity adjustment needed. As there may be practical limitations to the precision of movement of filter 112 across a given boundary, providing a filter with multiple regions that are variations on a particular color may facilitate more precise chromaticity adjustments.

Example 5C illustrates yet another configuration of filter 112. This example is similar to 5B, except that the lower region transmits a portion of the visible spectrum that includes blue, which may include wavelengths in the range of 420 nm to 495 nm. For example, the lower region may comprise a high-wavelength cutoff in the blue spectrum. Other examples may include a high-wavelength cutoff between the blue and red spectrum, or a high-wavelength cutoff in the red spectrum. By providing both a region that filters red and a region that filters blue, example 5B facilitates adjusting the chromaticity of a light beam toward to the left or right of FIG. 12 (redder or bluer). Such may be particularly useful in embodiments of system 100 that include only a single filter, or in combination with a second filter to fine-tune chromaticity within a target range Examples 5D and 5E are similar to 5A and 5B respectively, except that they include blue rather than red color regions. For instance, similar to example 5B, the top and lower regions of example 5E may transmit different portions of the visible spectrum that include blue, analogous to the blue region of FIG. 5C described above. Further, in certain embodiments, the upper region of FIG. 5E may comprise a high-wavelength cutoff at a particular wavelength zone (e.g., 495 nm), and the lower region may comprise a high-wavelength cutoff at a different wavelength zone (e.g., between 495 and 615 nm). Characteristics and benefits described above with respect to 5A and 5B thus apply analogously to 5D and 5E.

Example 5F is similar to 5C, except that the filter regions are separated by gradient areas 503 and 504, rather than distinct boundaries 501 and 502. In gradient areas 503 and 504, the transition from a first filter characteristic (e.g., red of FIG. 5A) in the upper region to clear in the center region, and from clear in the center region to a second filter characteristic (e.g., blue of FIG. 5D) in the lower region, may be continuous or incremental across areas 503 and 504. Areas 503 and 504 may comprise be any suitable size and shape to facilitate more precise adjustment of the chromaticity of light beam 104 impinging on filter 112. For example, as filter 112 is rotated about its center axis, each degree of rotation will result in a chromaticity adjustment to a light beam impinging on gradient areas 503 and 504 that may be more gradual than would be achieved with examples that include distinct boundaries. Gradient areas 503 and 504 may thus facilitate adjustments to transmittance characteristics and chromaticity of beam 104 in smaller increments than would be possible using a filter design with distinct boundaries between regions.

Figure 6:
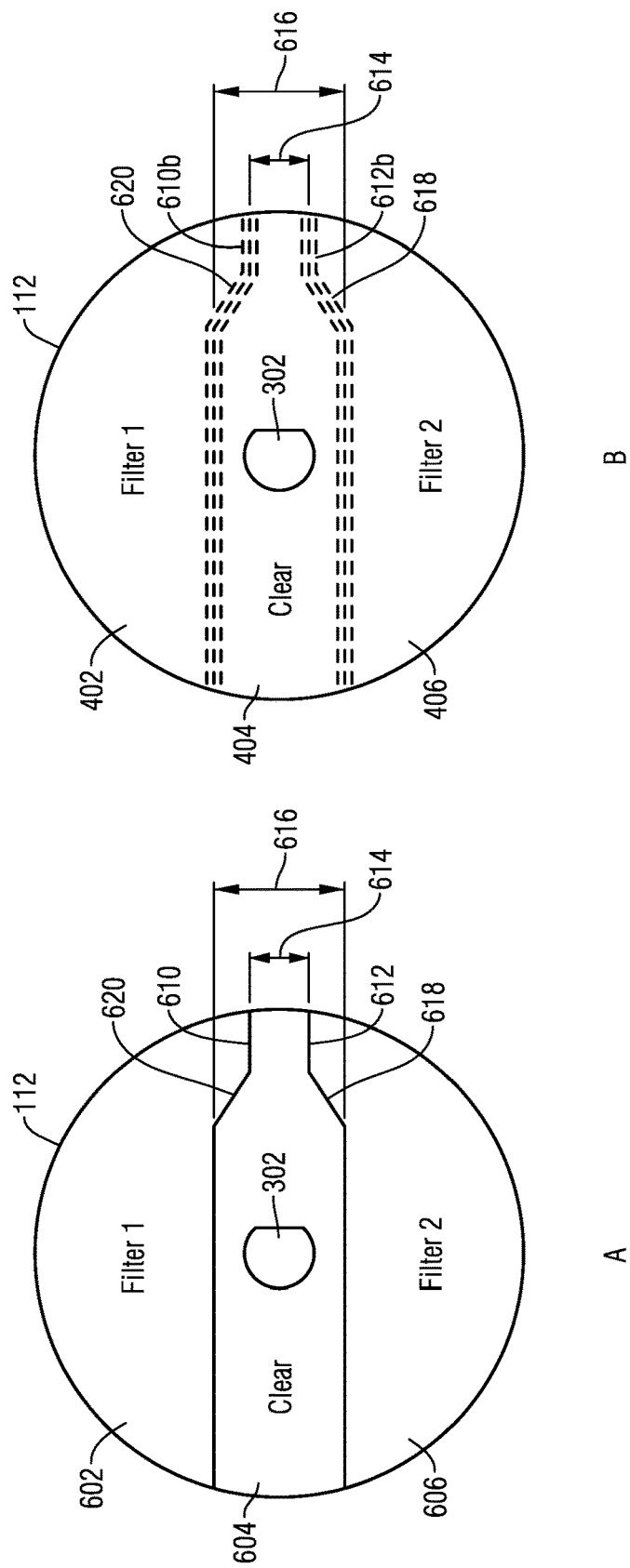

FIG. 6 illustrates examples of a filter wheel 112 in which a first region 602, second region 604, and third region 606 are separated by distinct boundaries 610 and 612 (FIG. 6A) or gradient boundaries 610 and 612 (FIG. 6B). Region 602 comprises a first filter, region 604 is clear, and region 606 comprises a second filter. The first and second filter regions may comprise any combination of spectral filtering characteristics (e.g., low-wavelength cutoff in blue, high-wavelength cutoff in red, high-wavelength cutoff in blue, and/or high-wavelength cutoff in red, or a cutoff in any intermediate spectral zone).

In the example of FIG. 6A, on the side to the left of orifice 408, boundary lines 610 and 612 are parallel and are separated by a distance 616. To the right of orifice 302, boundary lines 610 and 612 converge for a span at segments 618 and 620, such that the distance between them decreases to distance 614, where boundary lines 610 and 612 again run parallel to the edge of filter 112. The centerline of gradient regions 610b and 612b of example 6B are arranged in the same manner.

The left side of filter 112 in FIG. 6A provides similar characteristics and advantages as in FIGS. 5B, 5C, and 5E. Similarly, the left side of filter 112 in FIG. 6B provides similar characteristics and advantages as in FIG. 5F. Moreover, the angle of segments 618 and 620 on the right side of filter 112 in FIGS. 6A and 6B may permit more granular chromaticity adjustments, as discussed above with respect to FIG. 4B. As explained above, reducing the angle between a regional boundary on filter 112 and the direction of motion may reduce the motion of the boundary across the beam 104, given a fixed resolution/step. Thus, by presenting a reduced angle relative to rotational motion about orifice 308, segments 618 and 620 may reduce the motion of the boundary lines 610 and 612 across a laser beam 104 for a fixed step/adjustment. Moreover, configuring segments 618 and 620 as gradient areas as shown in FIG. 6B may permit even more gradual adjustments to chromaticity of light beam 104.

Figure 7:
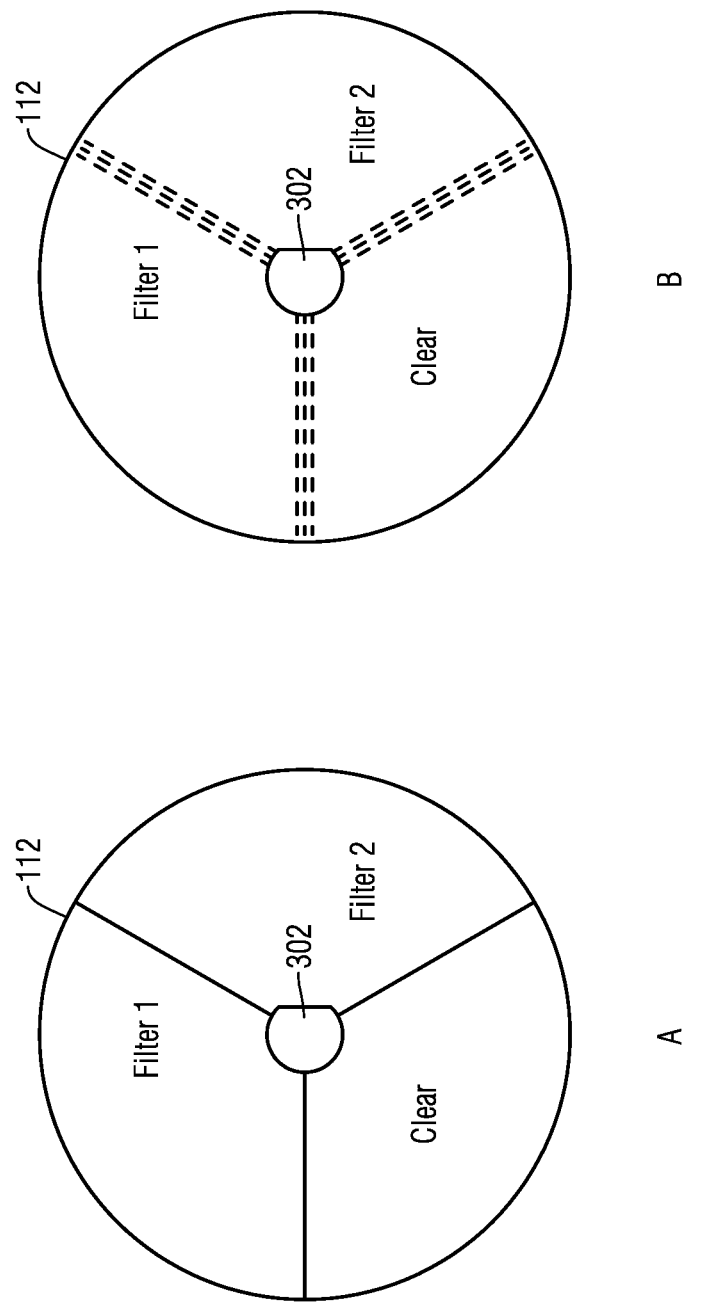

FIG. 7 illustrates examples of a filter wheel 112 in which three regions are arranged according to a pie configuration divided approximately in thirds, for use in certain embodiments of system 100. The configuration of FIG. 7 provides yet another variation of the angle between regional boundaries on filter 112 and the direction of motion, which may impact the granularity of chromaticity adjustments, as explained above.

Figure 8:
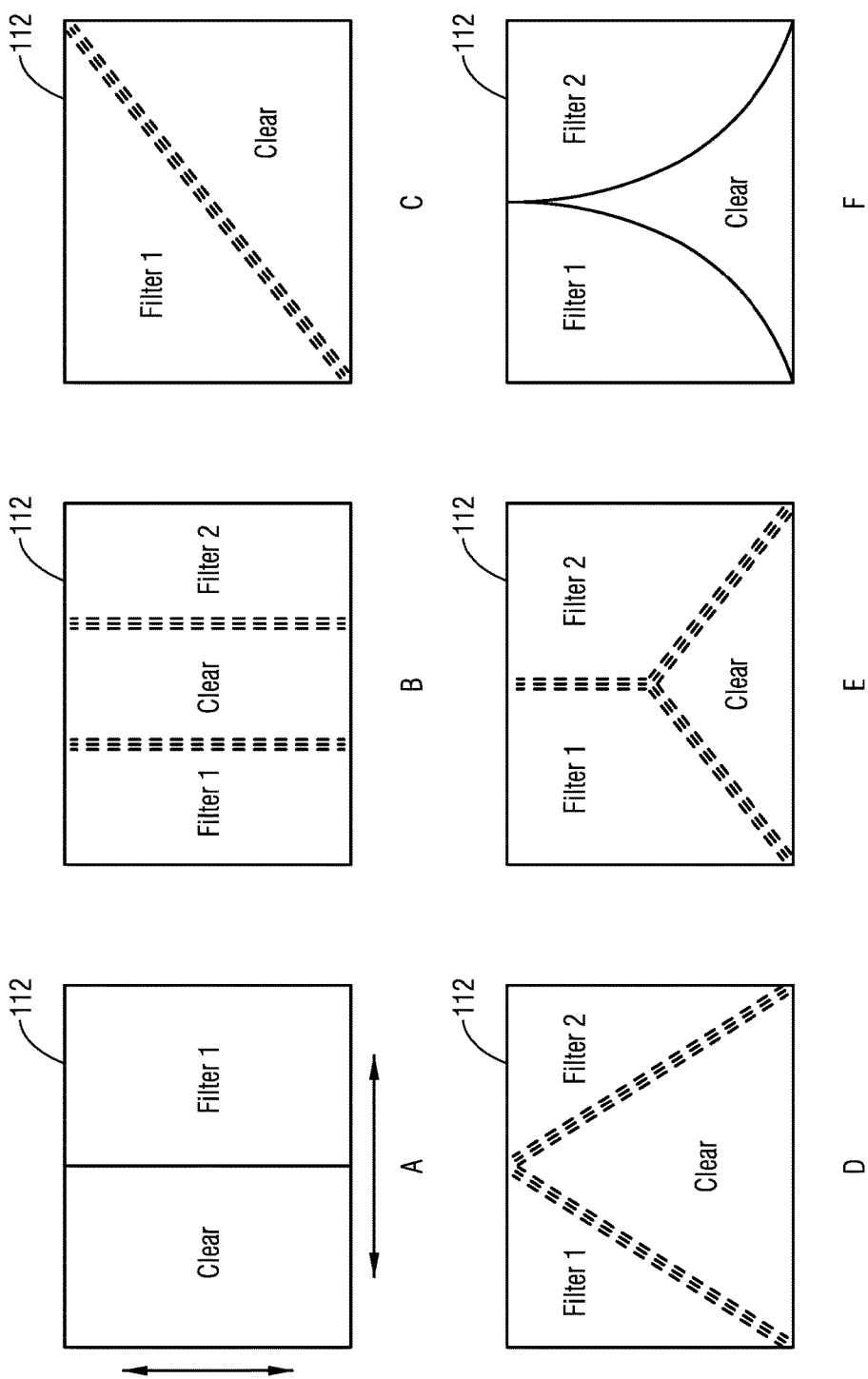

Although FIGS. 3-7 illustrate filter wheels configured to move rotationally about a center axis, the principles discussed herein apply analogously to filters that are otherwise moved (e.g., horizontally and/or vertically) with respect to an impinging light beam. For example, FIG. 8 illustrates examples of a rectangular filter 112 with two or three regions in various arrangements, according to certain embodiments of system 100. The designs depicted in FIG. 8 may be useful in embodiments of system 100 that actuate or reposition filter 112 using a motor or actuator configured to move filter 112 horizontally and/or vertically with respect to an impinging light beam 104 (rather than rotationally). Additionally, examples depicted in FIG. 8 include multiple variations of the angle between regional boundaries on filter 112 and a direction of motion, which may impact the granularity of chromaticity adjustments, as explained above. Again, the first and second filter regions may comprise any combination of spectral filtering characteristics.

Accordingly, FIGS. 5-8 illustrate example filter designs for use in certain embodiments. Further, it is understood that the filter designs illustrated in FIGS. 3-9 may comprise any suitable combinations of filter regions with different or like spectral filtering characteristics (e.g., bandpass filters, longpass filters, shortpass filters, notch filters, etc.) applicable to any zone of the visible spectrum. Moreover, one skilled in the art will recognize that principles discussed herein apply analogously to embodiments that include any number of filter designs, including filters having different divisional proportions, regions, spectral transmission characteristics, shapes, and colors.

Returning to FIG. 1, FIG. 1A illustrates an embodiment in which a single filter 112 is used to adjust and maintain chromaticity of light beam 104. Certain embodiments (including those in FIGS. 1B, 1C, and 1D), controller 136 may be configured to adjust chromaticity over a multi-dimensional chromaticity region, rather than a single chromaticity curve, by controlling a plurality of filters 112 and 114 that have spectral transmission characteristics. That is, the range of potential chromaticity adjustments of a light beam using a given filter region described above may be visualized as particular path through the (x,y) chromaticity space of FIG. 12. Typically, the path associated with a filter region is roughly a straight line. In the event greater flexibility is needed to adjust chromaticity over a two-dimensional region instead of a single line/curve, the beam may be passed through two transmission filters.

For example, certain embodiments may include identical filters 112 and 114 designed as shown in FIG. 6A or 6B (or any other figure), each of which include a clear region, a first filter region with a low wavelength cutoff zone in or near blue, and a second filter region with a high wavelength cutoff zone in or near red. Filters 112 and 114 may be independently manipulated such that laser beam 104 partially passes through the first filter region of filter 112 and the second filter region of filter 114, thereby adjusting the chromaticity of a laser beam 104 over an area (rather than simply across a line) of the chromaticity diagram of FIG. 12. Other examples may include a filter 112 with multiple low-wavelength cutoff regions in different parts of the visible spectrum and a filter 114 with multiple high-wavelength cutoff regions in different parts of the visible spectrum, arranged within the optical path of beam 104 and independently manipulated in a similar manner.

Figure 9:
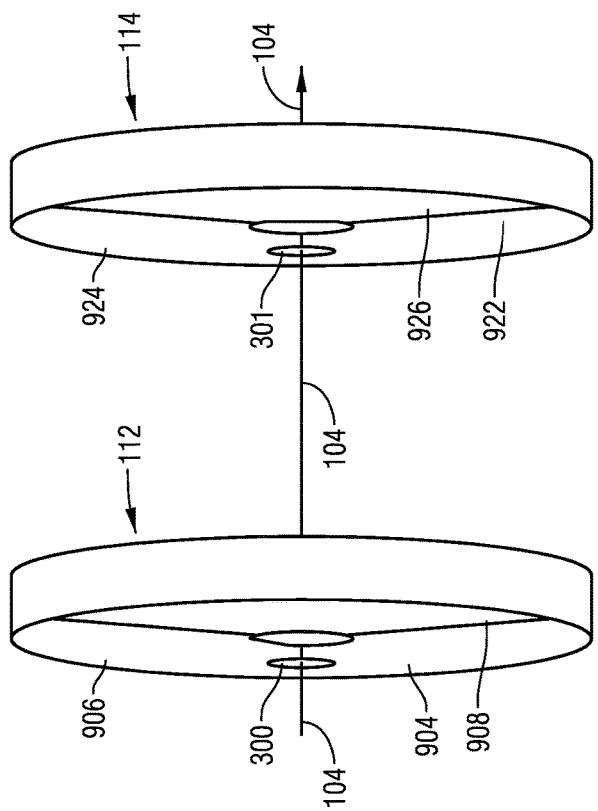
FIG. 9 illustrates an arrangement of two filters to control chromaticity of a light beam, according to certain embodiments.
Figure 9:
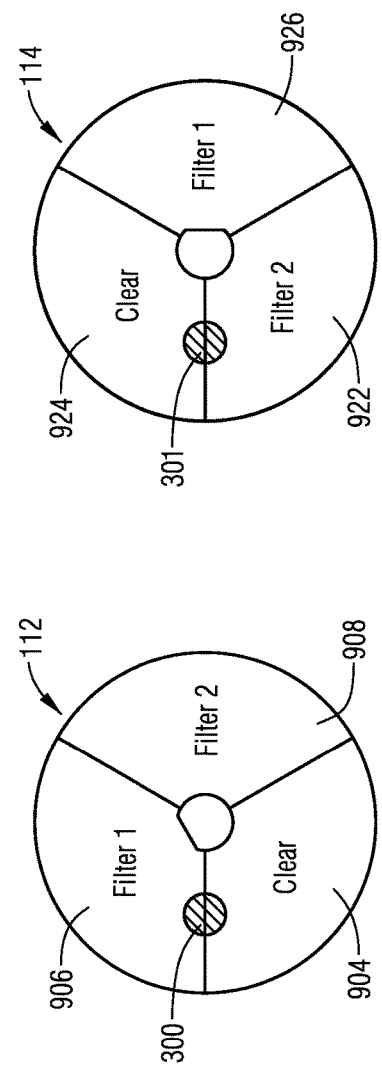

An example of a multi-filter configuration is illustrated in more detail in FIG. 9, which depicts first filter 112 and second filter 114 optically aligned to transmit light beam 104. Filter 112 is in FIG. 9 shown positioned such that light beam 104 impinges at point 300, across the boundary of clear region 904 and first filtered region 906. Assuming, for example, that region 906 comprises a low wavelength cutoff in blue, the chromaticity of light beam 104 will shift approximately towards the right (and perhaps toward the top or bottom as well) of FIG. 12 along a curve or line, in proportion to the fraction of beam 104 passing through each respective region.

Further, filter 114 is rotated such that light beam 104 impinges at point 301, which intersects the boundary between clear region 924 and second filter region 922. Assuming in this example that region 922 comprises a high wavelength cutoff in red, the chromaticity of light beam 104 will shift towards the left (and perhaps toward the top or bottom) of FIG. 12 along a different curve or line, in proportion to the fraction of beam 104 passing through region 922.

Depending on the characteristics of filters 112 and 114, as well as the target chromaticity adjustment for light beam 104, filters 112 and 114 may be rotationally adjusted to any suitable positions to cause light beam 104 to pass through all or part of any filter region, in any proportion or combination of such regions. In this manner, the chromaticity of beam 104 may be modified by one or both filters 112 and 114 to achieve a particular (x,y) chromaticity. Using both filters 112 and 114 may facilitate more precise chromaticity tuning, allowing the chromaticity value of the light beam to be adjusted along multiple filter rotational angle curves of FIG. 12, rather than a single curve, making it possible to exactly achieve a particular (x,y) chromaticity value. Moreover, any suitable filter design and regional filtering characteristics may be used in various embodiments. For example, filters 112 and 114 of FIG. 9 may utilize the filter design shown in FIG. 6, or any other design depicted in FIGS. 3-8, and may be identical or comprise different region designs or spectral filtering characteristics.

Figure 1B:
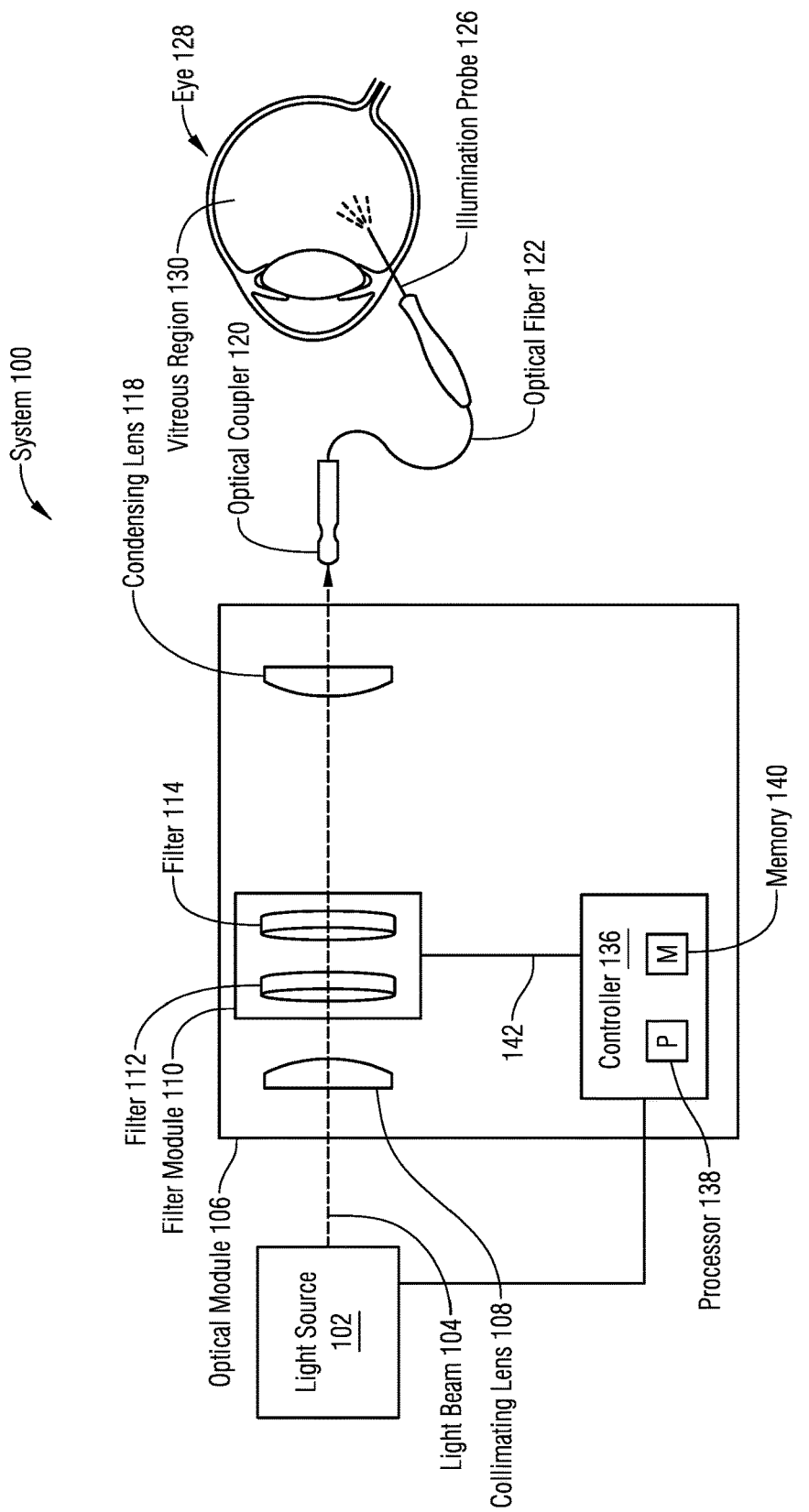

FIGS. 1A and 1B illustrate embodiments in which controller 136 is configured to automatically adjust or maintain the chromaticity of laser beam 104 by adjusting the position of filter 112 and/or 114 based on pre-stored data. For example, controller 136 may be configured to move one or more filters gradually over time, based on predefined operating-time/chromaticity shift data stored in memory 140, to yield near-constant chromaticity of beam 104. Similarly, embodiments of system 100 can automatically adjust the chromaticity of beam 104 based on stored data correlating laser engine power or emitted laser energy with chromaticity shift. Stored data may be loaded to memory 140 at the time of manufacture, or may be loaded and/or updated via a wired or wireless communication link with a remote system.

In certain embodiments, memory 140 may store data correlating cumulative operating time of light source 102 to an expected change in (x,y) chromaticity of beam 104. Stored correlation data may, for example, associate a plurality of (x,y) chromaticity change/shift values (e.g., $\Delta x$, $\Delta y$) to particular operating time milestones, such as hour-based milestones (e.g., every 10 hours, every 50 hours, every 100 hours, etc.). Stored correlation data may additionally or alternatively associate a plurality of absolute chromaticity values (e.g., $x_1$, $y_1$) to particular operating time milestones. Correlation data may be based on laboratory or real-world testing of light sources. For instance, based on testing of light sources representative of source 102, correlative data may specify that, at 50 hours of usage of source 102, the expected chromaticity of beam 104 is ($x_1$, $y_1$), or the expected chromaticity shift of beam 104 is ($\Delta x_1$, $\Delta y_1$); at 100 hours of usage, ($x_2$, $y_2$) or ($\Delta x_2$, $\Delta y_2$); at 150 hours, ($x_3$, $y_3$) or ($\Delta x_3$, $\Delta y_3$), etc.

Additionally or alternatively, memory 140 may store values specifying a positional shift for one or more dichroic filters that will compensate for the expected change in chromaticity of beam 104. For example, memory 140 may store a plurality of $\Delta \Theta$ values, each of which specifies a rotation of one or more individual filters (e.g., filter 112 and filter 114, shown in FIGS. 1C and 1D) to compensate for the expected chromaticity shift of beam 104 at a given time milestone. For instance, such data may specify that, at 50 hours of usage of source 102, the filters 112 and 114 are to be rotated by ($\Delta \Theta_{a1}$, $\Delta \Theta_{b1}$); at 100 hours of usage, ($\Delta \Theta_{a2}$, $\Delta \Theta_{b2}$); at 150 hours, ($\Delta \Theta_{a3}$, $\Delta \Theta_{b3}$), etc. In embodiments of system 100 in which filters are configured to move laterally, vertically, or otherwise, memory 140 may store values that specify such movements. In certain embodiments, processor 138 may calculate the positional shift for filter 112 to compensate for a given change in chromaticity of beam 104, based on an expected change in (x,y) chromaticity of beam 104.

Based on data stored in memory 140, processor 138 may send commands to adjust the one or more filters 112 and 114 according to stored or calculated positional shift values. In certain embodiments, processor 138 generates signals to control one or more step motors configured to rotate the filters according to a specified $\Delta\Theta$ value. In certain embodiments, processor 138 generates signals to separately control a plurality of step motors configured to rotate multiple filters independently. Processor 138 may generate signals to control others movement mechanisms as well, including but not limited to servomotors or other actuators.

Thus, in certain embodiments, controller 136 may store software in memory 140 that, when executed by processor 138, tracks the operating time of light source 102, identifies when cumulative operating time reaches a predefined milestone, and automatically moves one or more filters 112 and/or 114 to compensate for the expected chromaticity shift associated with that milestone, such that the chromaticity remains or returns to the white region of FIG. 12. This process may be executed continuously for a plurality of milestones such that filters 112 and 114 are gradually adjusted over time to maintain target chromaticity of light beam 104.

Although the above-described embodiments correlate a change in chromaticity with total operating hours, other correlative data may be used in various embodiments. For example, certain embodiments may store and implement chromaticity adjustments based on expected changes in laser engine power over time, or emitted laser energy over time.

Figure 10:
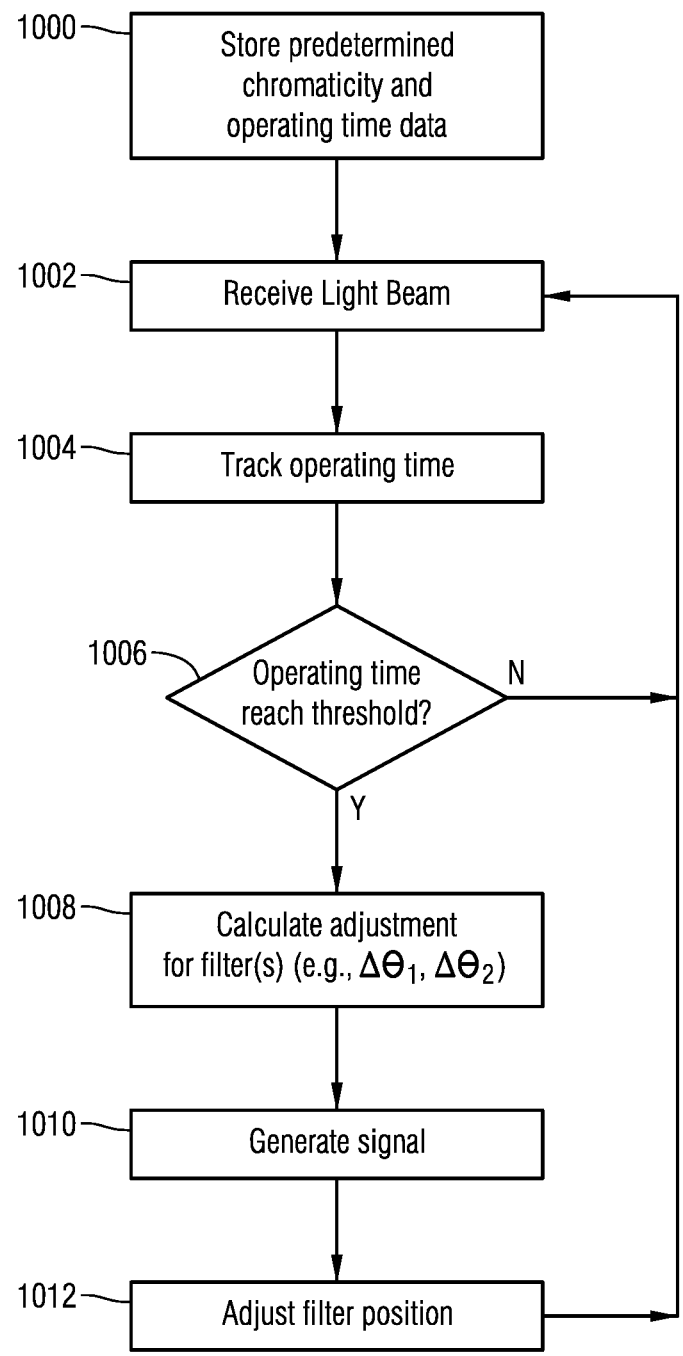
FIG. 10 illustrates a method for controlling chromaticity of a light beam based on pre-stored data, according to certain embodiments.

FIG. 10 is a flow chart describing the operation of certain embodiments of system 100 which automatically adjust chromaticity based on pre-stored data. At step 1000, data associating chromaticity shifts or adjustments and operating time for light source 102 is stored in memory 140 of controller 136. For example, memory 140 may store data correlating cumulative operating time of light source 102 to an expected or average chromaticity shift of beam 104 and/or a positional adjustment for filters 112 and/or 114. In one embodiment, memory 140 may store data specifying filter position adjustment value for 10-hour milestones:

| Cumulative Operating Time | Positional Adjustment Values |
|---|---|
| 10 hours | $\Delta\Theta_{a1}, \Delta\Theta_{b1}$ |
| 20 hours | $\Delta\Theta_{a2}, \Delta\Theta_{b2}$ |
| 30 hours | $\Delta\Theta_{a3}, \Delta\Theta_{b3}$ |
| ... | ... |

At step 1002, light beam 104 emitted by light source 102 is received at filter module 110. Controller 136 may be configured to determine when light source 102 is emitting light beam 104 in order to track usage time. In certain embodiments, controller 136 receives a signal when light source 102 begins emitting light beam 104.

At step 1004, having determined that light source 102 is emitting light beam 104, controller 136 begins tracking operating time of light source 102. Processor 138 and memory 140 may execute instructions to track cumulative operating time of light source 102, as well as the length of individual uses/sessions during which light source 102 is emitting beam 104. Operating time may be tracked in any suitable increments, e.g., seconds, minutes, hours, etc.

At step 1006, controller 136 checks whether the tracked operating time reaches a threshold or milestone. Processor 138 may execute instructions to compare tracked operating time with predetermined chromaticity and operating time data stored in memory 140. For example, processor 138 may execute a software program which tracks operating time and periodically checks to determine whether total operating time has reached an hours-based threshold, e.g., 10 hours, 20 hours, etc. If not, the system returns to step 1002. If, however, the operating time has reached a predetermined threshold, system 100 proceeds to step 1008.

At step 1008, controller 136 determines an adjustment for filters 112 and/or 114. In certain embodiments, processor 138 may calculate angular, lateral, and/or vertical adjustment values for filters 112 and/or 114 based on pre-stored chromaticity shift data associated with the operating time threshold reached at step 1006. In certain embodiments, processor 138 may retrieve and/or translate pre-stored data that specifies angular, lateral, and/or vertical adjustment values for filters 112 and/or 114.

At step 1010, controller 136 generates a signal to cause filters 112 and/or 114 to move according to the determined adjustment values. Controller 136 communicate a signal to cause electromechanical components of filter module 110, such as motors and/or actuators, to adjust filters 112 and/or 114 to compensate for the expected chromaticity shift of beam 104 associated with the operating time threshold reached at step 1006. At step 1012, motors and/or actuators in filter module 110 move filters 112 and/or 114 according to the signal received from controller 136. The process may then return to step 1002.

Figure 1C:
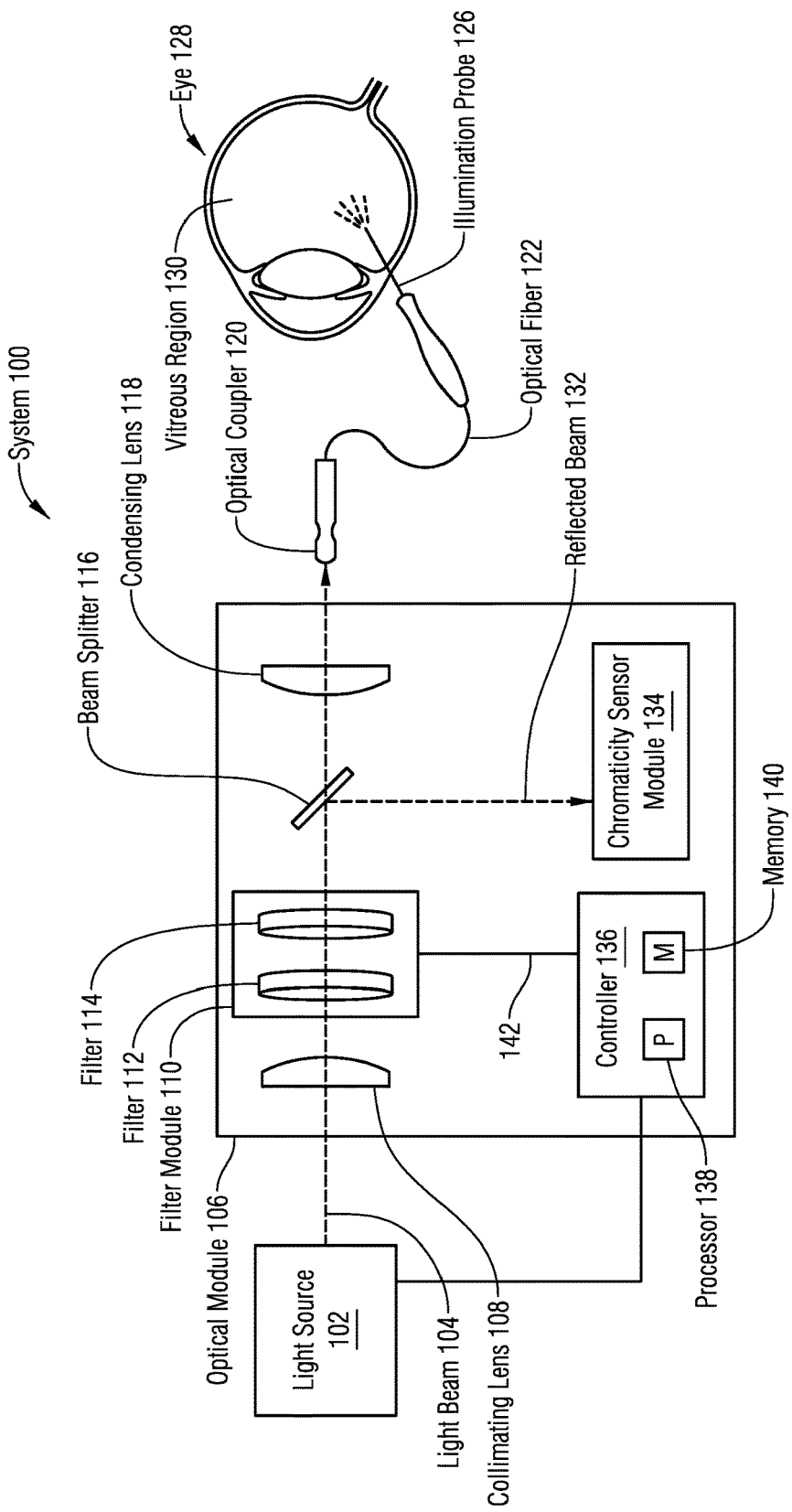
Figure 1D:
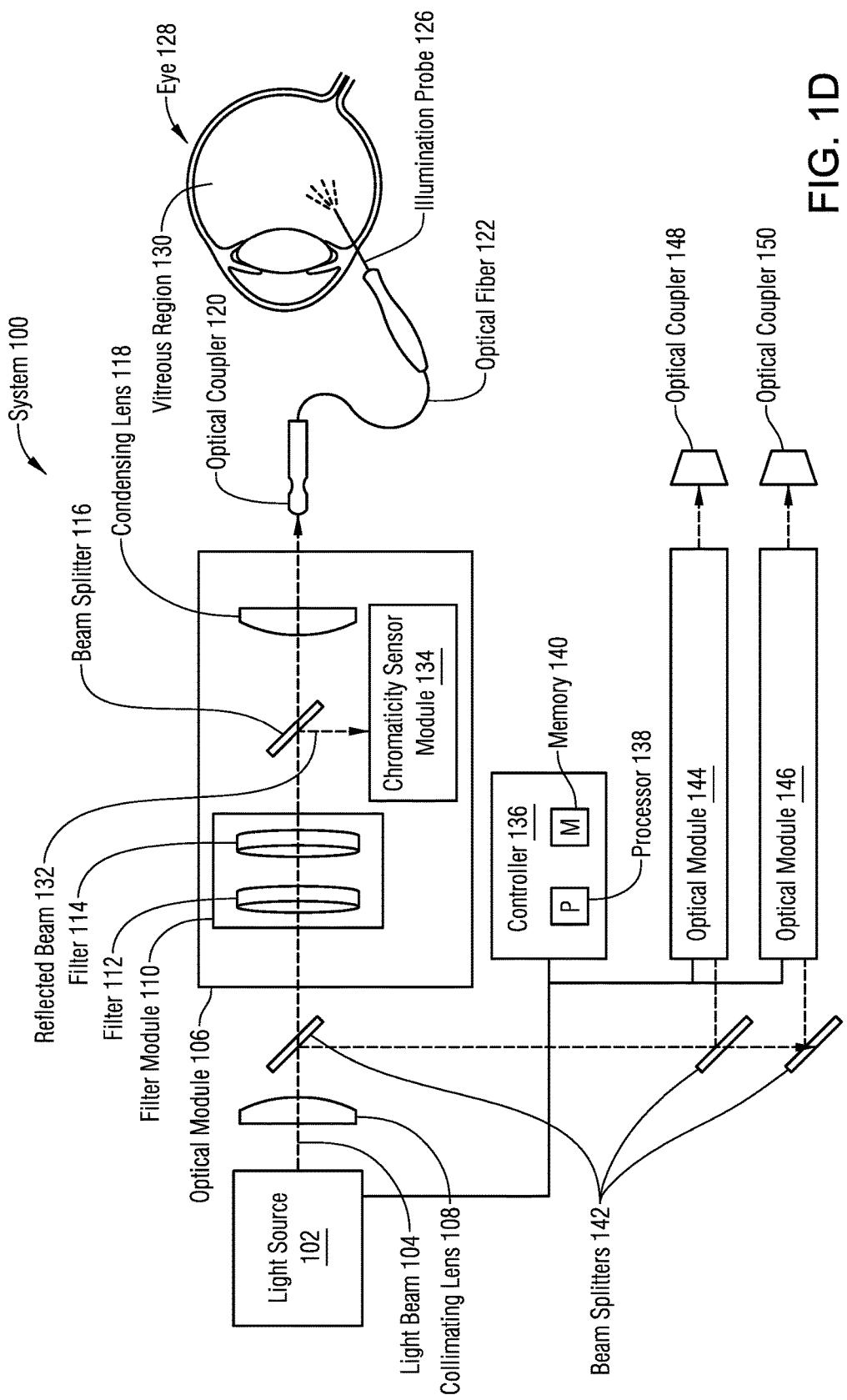

Rather than adjusting filters based on pre-loaded data, certain embodiments of system 100 may adjust filters based on real-time measurements of actual chromaticity. FIGS. 1C and 1D illustrate embodiments in which controller 136 is configured to automatically control the chromaticity of laser beam 104 based on actual measured chromaticity of the laser beam 104. In addition to components and features shown in FIGS. 1A and 1B, such embodiments may include a beam splitter 116 configured to reflect a portion of laser beam 104 to a chromaticity sensor module 134 coupled to controller 136. In such embodiments, controller 136 may use active feedback from chromaticity sensors to ensure that one or more dichroic filters 112 and 114 are positioned to maintain a target chromaticity of the laser beam 104. Although filter module and beam splitter are shown positioned between the collimating lens and condensing lens, they may be arranged anywhere in optical path of light beam 104.

Figure 2:
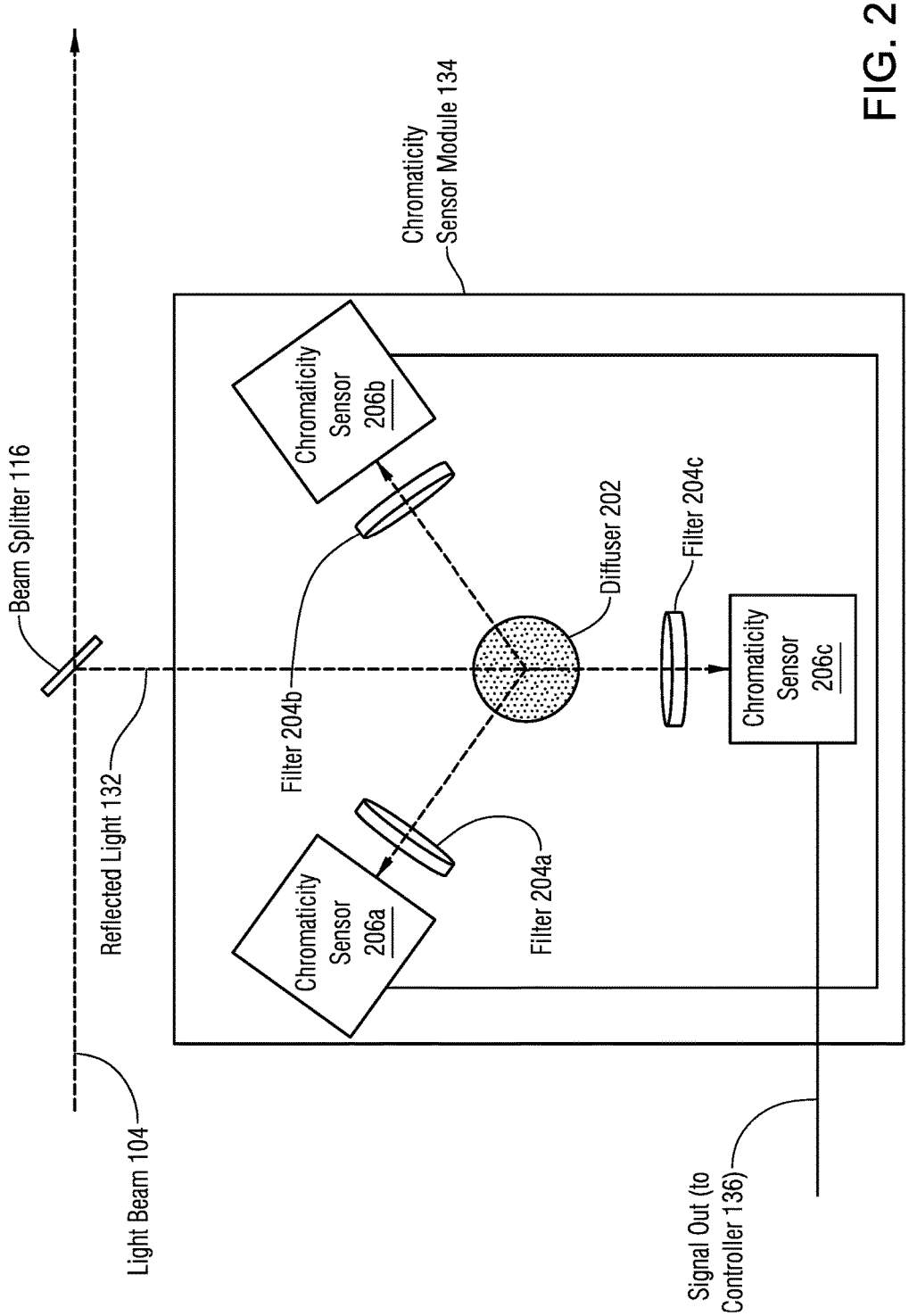
FIG. 2 illustrates a chromaticity sensor module, according to certain embodiments.

FIG. 2 illustrates chromaticity sensor module 134 in additional detail, according to certain embodiments. Chromaticity sensor module is configured to measure the chromaticity of reflected light 132 (which is the same as the chromaticity of light beam 104 as it exits filter module 110) and output a signal to controller 136 which indicates the measured chromaticity. In operation, beam splitter 116 directs reflected light 132 to a diffuser 202 (e.g., a lambertian diffuser) arranged to diffuse reflected light 132 toward a plurality of filters 204 and chromaticity sensors 206. Filters 204 and chromaticity sensors 206 may be symmetrically arranged around diffuser 202, and are configured to receive reflected light 132 and generate a signal indicating the chromaticity of light 132. Certain embodiments may include three chromaticity sensors 206a-c, each associated with a different color filter 204a-c. For example, filters 204a, 204b, and 204c may be designed to correspond to the X-bar, Y-bar, and Z-bar tristimulus function, respectively. Filters 204 are located between sensors 206 and diffuser 202, within the optical path of reflected light 132 received from diffuser 202. Accordingly, each sensor 206a-c receives reflected light 132 through an associated filter 204a-c, proportional to the color value X, Y, and Z, where the (x,y) chromaticity values are calculated by:

$$x = \frac{X}{X+Y+Z}$$
$$y = \frac{Y}{X+Y+Z}$$

Based on a measurement response to received light 132, each chromaticity sensor 206 generates a signal that indicates a detected color or chromaticity value of the filtered reflected light 132 (e.g., a chromaticity (x,y) value or tristimulus XYZ value) and outputs the signal to controller 136, which may be communicatively coupled to chromaticity sensor module 134 via wired or wireless connection. Sensors 206 may each be precalibrated using a beam of known (x,y) chromaticity to ensure the chromatic accuracy. Sensors 206 are configured to provide chromaticity signals in real-time so that controller 136 can actively adjust and maintain chromaticity of light beam 104.

Although FIG. 2 illustrates three chromaticity sensors 206, other embodiments may utilize more or fewer chromaticity sensor(s). Certain embodiments may utilize one or more chromaticity sensors configured to receive reflected light 132 directly, rather than via a diffuser and/or filter, and generate signals indicating the chromaticity of reflected slight 132 for output to controller 136.

In certain embodiments, controller 136 receives signals from one or more sensors 206 of chromaticity sensor module 134 and, based on the signals, control the chromaticity of light beam 104 by adjusting components of filter module 110. Processor 138 and memory 140 may work together to automatically control and adjust the chromaticity of a laser beam based on a direct real-time chromaticity measurement of the laser beam.

In certain embodiments, memory 140 stores target chromaticity values for light beam 104. For example, memory 140 may store target chromaticity (x,y) values or target tristimulus XYZ values corresponding to white for a supercontinuum laser beam 102. In certain embodiments, target values may comprise a range of values.

Signals generated by chromaticity sensor module 134 may be received by controller 136 and stored in memory 140. Processor 138 may execute software instructions to compare detected real-time chromaticity values received from sensor module 134 with target chromaticity values stored in memory 140 to calculate the difference between them, if any. In certain embodiments, processor 138 executes an algorithm to compute a difference between actual and target chromaticity values.

In the event processor 138 determines that actual chromaticity of beam 104 deviates from a target chromaticity value or range, it may additionally execute an algorithm to determine positional adjustment values for filters 112 and 114 necessary to adjust or maintain actual chromaticity of beam 104 at a target value or range. For example, processor 138 processes a calculated $\Delta x$, $\Delta y$ chromaticity value difference to determine a $\Delta\Theta_1$ and $\Delta\Theta_2$, where $\Delta\Theta_1$ is an angle of rotation for filter 112 and $\Delta\Theta_2$ is an angle of rotation for filter 114 that together will cause the chromaticity of light beam 104 exiting filter module 110 to align with a target value or fall within a target range. In certain embodiments, processor 138 may execute an algorithm to translate a calculated $\Delta x$, $\Delta y$ chromaticity value to horizontal and/or vertical positional adjustment values for filters 112 and/or 114 necessary to adjust or maintain actual chromaticity of beam 104 at a target value or range. Algorithms used to determine positional adjustment for filters 112 and 114 will be calibrated to account for the specific characteristics of the filters, including but not limited to the size, shape, layout, regional boundaries or gradient zones, angle and direction of movement, color, and/or spectral filtering characteristics of each filter.

Processor 138 may additionally generate a signal to cause a motor or actuator to move filter 112 and/or 114 according to determined positional adjustment values. Accordingly, certain embodiments of system 100 are configured to move or adjust filters 112 and/or 114 based on the actual chromaticity (measured in real time) of light beam 104, in order to continuously adjust or maintain a target chromaticity value or range. Active feedback from chromaticity sensors may be used by controller 136 to ensure that, as one or more dichroic filters are adjusted (e.g., rotated, or translated laterally or vertically), a target chromaticity of the laser beam is actively maintained.

Figure 11:
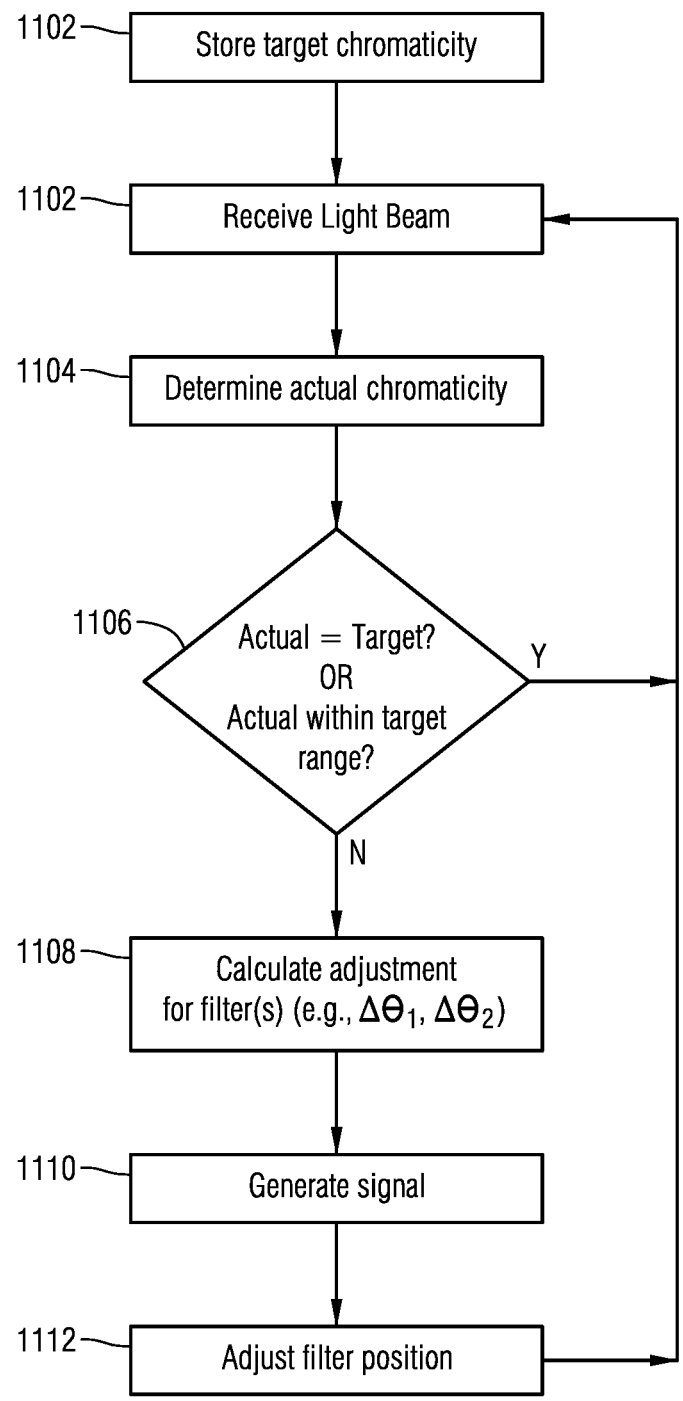
FIG. 11 illustrates a method for controlling chromaticity of a light beam based on real-time chromaticity measurements, according to certain embodiments.

FIG. 11 is a flow chart of a process for actively maintaining a target chromaticity based on real-time chromaticity measurements, according to certain embodiments. At step 1100, data identifying target chromaticity values or a target chromaticity range for light beam 104 is stored in memory 140 of controller 136. For example, memory 140 may store data specifying a specific (x,y) chromaticity value, or range of (x,y) chromaticity values (e.g., an area) in the white region of the chromaticity diagram depicted in FIG. 12.

At step 1102, light beam 104 emitted by light source 102 is received at filter module 110. Controller 136 may be configured to determine when light source 102 is emitting light beam 104 in order to track usage time. In certain embodiments, controller 136 receives a signal when light source 102 begins emitting light beam 104.

At step 1104, controller 136 receives one or more signals from chromaticity sensor module 134 indicating measured chromaticity of light beam 102.

At step 1106, controller 136 determines if the measured chromaticity of light beam 102 is equal to or within range of a target chromaticity. Processor 138 and memory 140 may execute instructions to compare a target chromaticity value with a measured chromaticity value indicated by the signal received from sensor module 134. In certain embodiments, processor 138 and memory 140 may execute instructions to compare a target chromaticity range with a measured chromaticity value. If it is determined that the measured chromaticity is equal to a target chromaticity value or falls within a target chromaticity range, the process returns to step 1102. If not, the process proceeds to step 1108.

At step 1108, controller 136 calculates positional adjustment values for filters 112 and/or 114 to adjust the chromaticity of beam 104 to a target value or range. For example, processor 136 may determine that filters 112 and/or 114 should be rotated by angles $\Delta\Theta_1$ and $\Delta\Theta_2$, respectively, to restore the chromaticity of beam 104 to a target range. Processor 136 may be programmed to account specific characteristics of the filters being used. That is, the particular algorithms executed by processor 136 may include constants, inputs, and variables tailored for specific filter designs.

At step 1110, controller 136 generates and sends a signal to control filters 112 and/or 114. Controller 136 may communicate a signal to cause electromechanical components of filter module 110, such as motors and/or actuators, to adjust filters 112 and/or 114 according to the adjustment calculated at step 1108. At step 1012, motors and/or actuators in filter module 110 move filters 112 and/or 114 according to the signal received from controller 136. The process may then return to step 1002.

FIG. 1D illustrates an embodiment of system 100 which includes the features and components discussed in FIG. 1C. However, system 100 in FIG. 1D further includes additional optical modules 144 and 146 communicatively coupled to controller 136 and light sourced 102. Optical modules 144 and 146 each include components analogous to those shown and discussed in optical module 106. Each of optical modules 106, 144 and 146 receive light beam 104 emitted by light source 102, by way of one or more beam splitters 142. Moreover, optical module 144 and 146 area each associated with optical coupler 148 and 150, respectively, which are analogous to optical coupler 120. Accordingly, embodiments depicted in FIG. 1D facilitate chromaticity control over multiple optical modules simultaneously. Such embodiments may facilitate uniquely adjusting the chromaticity of multiple illumination probes or other illumination instruments which share a single light source. In alternative embodiments, filter module 110, beam splitter 116, and chromaticity sensor module 134 may be located outside of optical modules 106, 144, and 146, such as between collimating lens 108 and beam splitters 142. In such embodiments, chromaticity of light source 102 may be controlled at a single point for transmission to multiple optical modules and illumination instruments.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An ophthalmic illumination system, comprising:
   a supercontinuum laser configured to emit a white laser beam;
   a first filter and a second filter arranged within an optical path of the white laser beam, wherein:
   the first filter comprises a first unfiltered region configured to transmit visible light in a visible spectrum, a first filtered region configured to transmit visible light in a first spectral range, and a second filtered region configured to transmit visible light in a second spectral range;
   the second filter comprises a second unfiltered region configured to transmit visible light in the visible spectrum, a third filtered region configured to transmit visible light in a third spectral range, and a fourth filtered region configured to transmit visible light in a fourth spectral range; and
   the first filter and the second filter are independently moveable to adjust chromaticity of a light beam in a complementary or additive manner with each other;
   a plurality of chromaticity sensors, each configured to:
   receive a portion of the laser beam transmitted by the first and second filters; and
   output a signal indicating a chromaticity value for the received portion of the beam; and
   a processor configured to:
   receive the signals output by the plurality of chromaticity sensors;
   compare the indicated chromaticity values to one or more target chromaticity values stored in memory;
   based on the comparison, adjust the chromaticity of the light beam transmitted by the filters by selecting the first and/or second filter to move and generating a signal to move the first and/or second filter such that the laser beam is partially incident on an unfiltered region and one of the filtered regions.

2. The ophthalmic illumination system of claim 1, wherein the signal indicating a chromaticity value of the laser beam output by each chromaticity sensor corresponds to a value for an X-bar, Y-bar, or Z-bar tristimulus function.

3. The ophthalmic illumination system of claim 1, wherein the first unfiltered region and the first filtered region are separated by a distinct boundary.

4. The ophthalmic illumination system of claim 3, wherein the distinct boundary comprises a line nonperpendicular to a direction of motion of the first filter.

5. The ophthalmic illumination system of claim 1, wherein the first unfiltered region and the first filtered region are separated by a gradient region which transitions from clear to the first filtered region.

6. The ophthalmic illumination system of claim 5, wherein the gradient region is situated around a centerline extending nonperpendicular to a direction of motion of the first filter.

7. The ophthalmic illumination system of claim 1, wherein the first or second filter is moved rotationally.

8. The ophthalmic illumination system of claim 1, wherein the first or second filter is moved horizontally or vertically.

9. An ophthalmic illumination system, comprising:
   a light source configured to emit a light beam;
   a first filter comprising a first clear region configured to transmit visible light in a visible spectrum and a first filtered region configured to transmit visible light in a first spectral range, the filter arranged within an optical path of the light beam;
   a second filter, independently movable from the first filter, wherein the second filter comprises a second clear region configured to transmit visible light in the visible spectrum and a second filtered region configured to transmit visible light in a second spectral range, the second filter arranged downstream of the first filter in the optical path of the light beam; and
   a plurality of chromaticity sensors, each configured to:
   receive a portion of the light beam transmitted by the first and second filters; and
   output a signal indicating a chromaticity of the received portion of the light beam; and
   a processor configured to:
   receive the signal indicating a chromaticity of the light beam from the chromaticity sensors;
   compare the indicated chromaticity of the light beam to a target chromaticity stored in memory; and
   based on the comparison, adjust the chromaticity of the light beam transmitted by the first and second filters by selecting the first and/or second filter to move and generating a signal to move the first and/or second filter from a first position to a second position such that the first filter and the second filter adjust chromaticity of the light beam in a complementary or additive manner with each other.

10. The ophthalmic illumination system of claim 9, wherein the signal indicating a chromaticity of the light beam output by each chromaticity sensor corresponds to a value for an X-bar, Y-bar, or Z-bar tristimulus function.

11. The ophthalmic illumination system of claim 9, wherein the first clear region and the first filtered region are separated by a distinct boundary.

12. The ophthalmic illumination system of claim 11, wherein the distinct boundary comprises a line nonperpendicular to a direction of motion of the filter.

13. The ophthalmic illumination system of claim 9, wherein the first filter is moved rotationally.

14. The ophthalmic illumination system of claim 9, wherein the first filter is moved horizontally or vertically.

15. The ophthalmic illumination system of claim 9, wherein the light source is a supercontinuum laser configured to emit a white laser beam.

16. The ophthalmic illumination system of claim 9, wherein the first spectral range includes wavelengths between 615 and 785 nm.

17. The ophthalmic illumination system of claim 9, wherein the first spectral range includes wavelengths between 420 and 495 nm.

18. The ophthalmic illumination system of claim 9, wherein the first filter further comprises a third filtered region configured to transmit visible light in a third spectral range.

19. An ophthalmic illumination system, comprising:
a supercontinuum laser configured to emit a white laser beam;
a first filter and a second filter arranged within an optical path of the white laser beam, wherein:
the first filter comprises a first unfiltered region configured to transmit visible light in a visible spectrum, a first filtered region configured to transmit visible light in a first spectral range, and a second filtered region configured to transmit visible light in a second spectral range;
the second filter comprises a second unfiltered region configured to transmit visible light in the visible spectrum, a third filtered region configured to transmit visible light in a third spectral range, and a fourth filtered region configured to transmit visible light in a fourth spectral range; and
the first filter and the second filter are independently moveable to adjust chromaticity of a light beam in a complementary or additive manner with each other;
a plurality of chromaticity sensors, each configured to:
receive a portion of the laser beam transmitted by the first and second filters; and
output a signal indicating a chromaticity value for the received portion of the beam; and
a processor configured to:
track cumulative operating time of the light source; and
based on the tracked cumulative operating time, adjust the chromaticity of the light beam transmitted by the first and second filters by selecting the first and/or second filter to move and generating a signal to move the first and/or second filter from a first position to a second position such that the first filter and the second filter adjust chromaticity of the light beam in a complementary or additive manner with each other.

* * * * *